(12) United States Patent
Ash et al.

(10) Patent No.: US 10,668,098 B2
(45) Date of Patent: Jun. 2, 2020

(54) ORAL SORBENT FOR REMOVING TOXINS OF KIDNEY FAILURE COMBINING ANION AND CATION EXCHANGERS

(71) Applicant: HEMOCLEANSE, INC., Lafayette, IN (US)

(72) Inventors: Stephen Richard Ash, Lafayette, IN (US); David John Carr, West Lafayette, IN (US)

(73) Assignee: HEMOCLEANSE TECHNOLOGY LLC, Lafayette, IN (US)

( * ) Notice: Subject to any disclaimer, the term of this patent is extended or adjusted under 35 U.S.C. 154(b) by 0 days.

(21) Appl. No.: 16/020,993

(22) Filed: Jun. 27, 2018

(65) Prior Publication Data
US 2019/0008894 A1   Jan. 10, 2019

Related U.S. Application Data

(60) Provisional application No. 62/529,580, filed on Jul. 7, 2017.

(51) Int. Cl.
| | |
|---|---|
| *A61K 31/795* | (2006.01) |
| *A61K 33/42* | (2006.01) |
| *A61K 9/14* | (2006.01) |
| *A61P 39/00* | (2006.01) |
| *A61K 33/24* | (2019.01) |
| *A61K 9/00* | (2006.01) |

(52) U.S. Cl.
CPC .......... *A61K 31/795* (2013.01); *A61K 9/0053* (2013.01); *A61K 9/14* (2013.01); *A61K 33/24* (2013.01); *A61K 33/42* (2013.01); *A61P 39/00* (2018.01); *A61K 2121/00* (2013.01)

(58) Field of Classification Search
CPC .... A61K 31/795; A61K 33/42; A61K 9/0053; A61K 33/24; A61K 9/14; A61K 2121/00; A61P 39/00
See application file for complete search history.

(56) References Cited

U.S. PATENT DOCUMENTS

| | | | |
|---|---|---|---|
| 8,802,152 B2 | 8/2014 | Keyser et al. | |
| 8,808,750 B2 | 8/2014 | Keyser et al. | |

FOREIGN PATENT DOCUMENTS

WO    WO 2015070019 A1 *   5/2015

OTHER PUBLICATIONS

Packhan et al., "Sodium Zirconium Cyclosilicate in Hyperkalemia" in The New England Journal of Medicine, Jan. 15, 2015.*
David J. Carr,"Zirconium Phosphate Multi-Ion Exchange Summary ZP and ZO Combination for Therapeutic Electrolyte Balancing", a Report Jul. 19, 2017.
Ash, Stephen R. "Innovation in the Treatment of Uremia: Proceedings from the Cleveland Clinic Workshop: Sorbents in Treatment of Uremia: A Short History and a Great Future." Seminars in dialysis. vol. 22. No. 6. Blackwell Publishing Ltd, 2009.
Flinn, Robert B., et al. "Treatment of the oliguric patient with a new sodium-exchange resin and sorbitol: a preliminary report." New England Journal of Medicine 264.3 (1961): 111-115.

(Continued)

*Primary Examiner* — Blessing M Fubara
(74) *Attorney, Agent, or Firm* — D'Hue Law LLC; Cedric A. D'Hue

(57) ABSTRACT

Oral sorbent compositions that bind small and charged toxins and methods of use.

14 Claims, 20 Drawing Sheets

(56) References Cited

OTHER PUBLICATIONS

Mahoney, Brian A., et al. "Emergency interventions for hyperkalaemia." The Cochrane Library (2005).
Kovesdy, Csaba P. "Management of hyperkalaemia in chronic kidney disease." Nature Reviews Nephrology 10.11 (2014): 653.
Danowski, T. S., et al. "Carboxylic cation exchange resin effects in dogs." The Journal of clinical investigation 30.9 (1951): 984-994.
Tomino, Y., et al. "Dose-response to a jelly preparation of calcium polystyrene sulfonate in patients with hyperkalemia—changes in serum potassium levels with or without a RAAS inhibitor." Clinical nephrology 68.6 (2007): 379-385.
Ash, S., et al. "Safety and efficacy of ZS-9, a novel selective cation trap, for treatment of hyperkalemia in CKD Patients." J Am Soc Nephrol 24 (2013): 2B.
Ash, Stephen R., et al. "A phase 2 study on the treatment of hyperkalemia in patients with chronic kidney disease suggests that the selective potassium trap, ZS-9, is safe and efficient." Kidney international 88.2 (2015): 404-411.
Wrong, O., and A. Metcalfe-Gibson. "The Electrolyte Content Faeces." Proceedings of the Royal Society of Medicine 58.12 (1965): 1007-1009.
Richards, Peter, M. B. S. Jones, and W. S. Peart. "Periodic hypokalaemic paralysis, adrenal adenoma, and normal colonic transport of sodium and potassium." Gut 14.6 (1973): 478-484.
BWB Technologies flame photometer, https://www.bwbtech.com/flame-photometer, as printed May 26, 2018, 4 pages.
Calcium Reagent Set, https://www.tecodiagnostics.com/calcium, as printed May 26, 2018, 2 pages.
Helfferich, Friedrich G. Ion exchange. Courier Corporation, 1962, pp. 78-94, 125-203, and 228-243.

\* cited by examiner

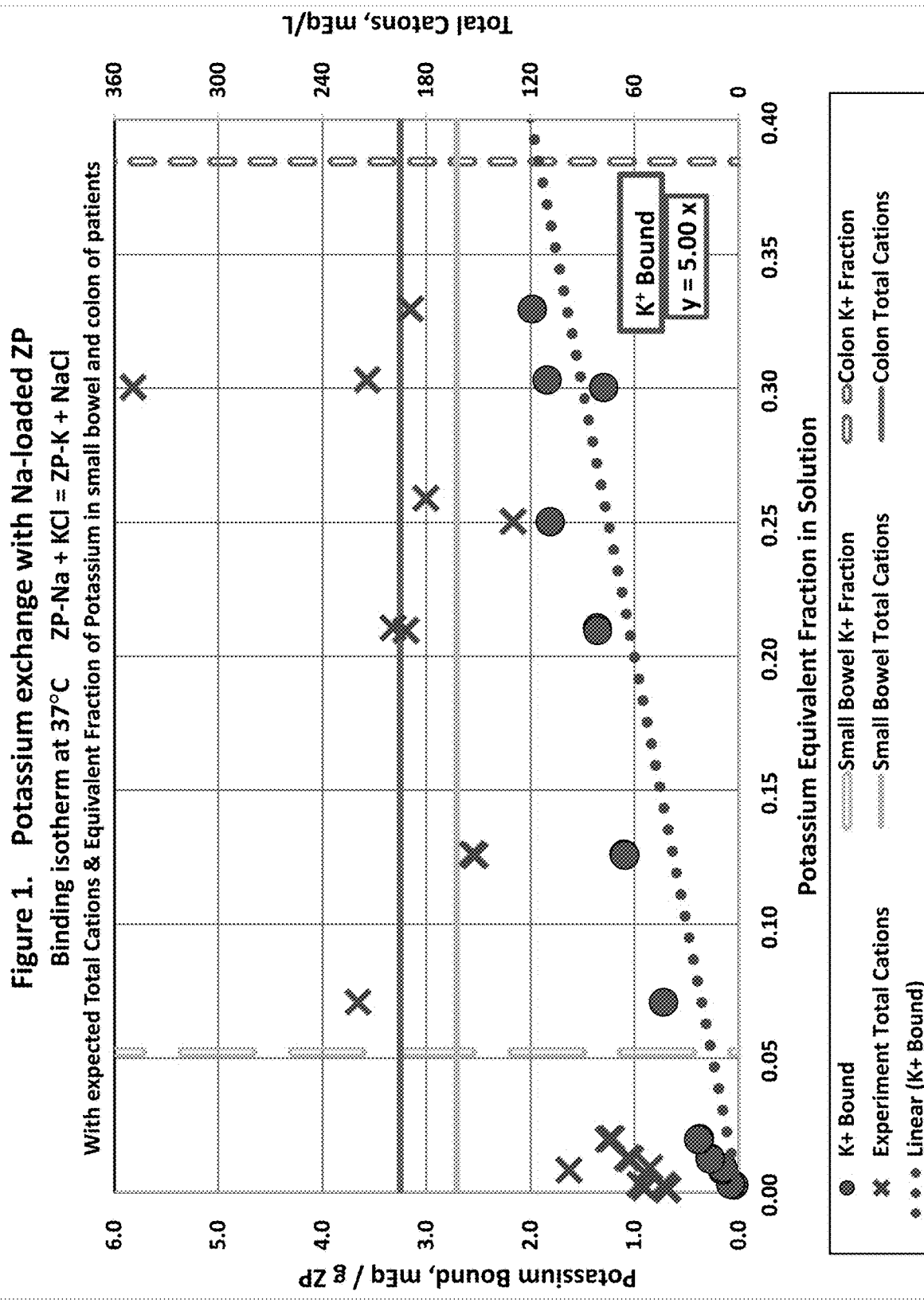

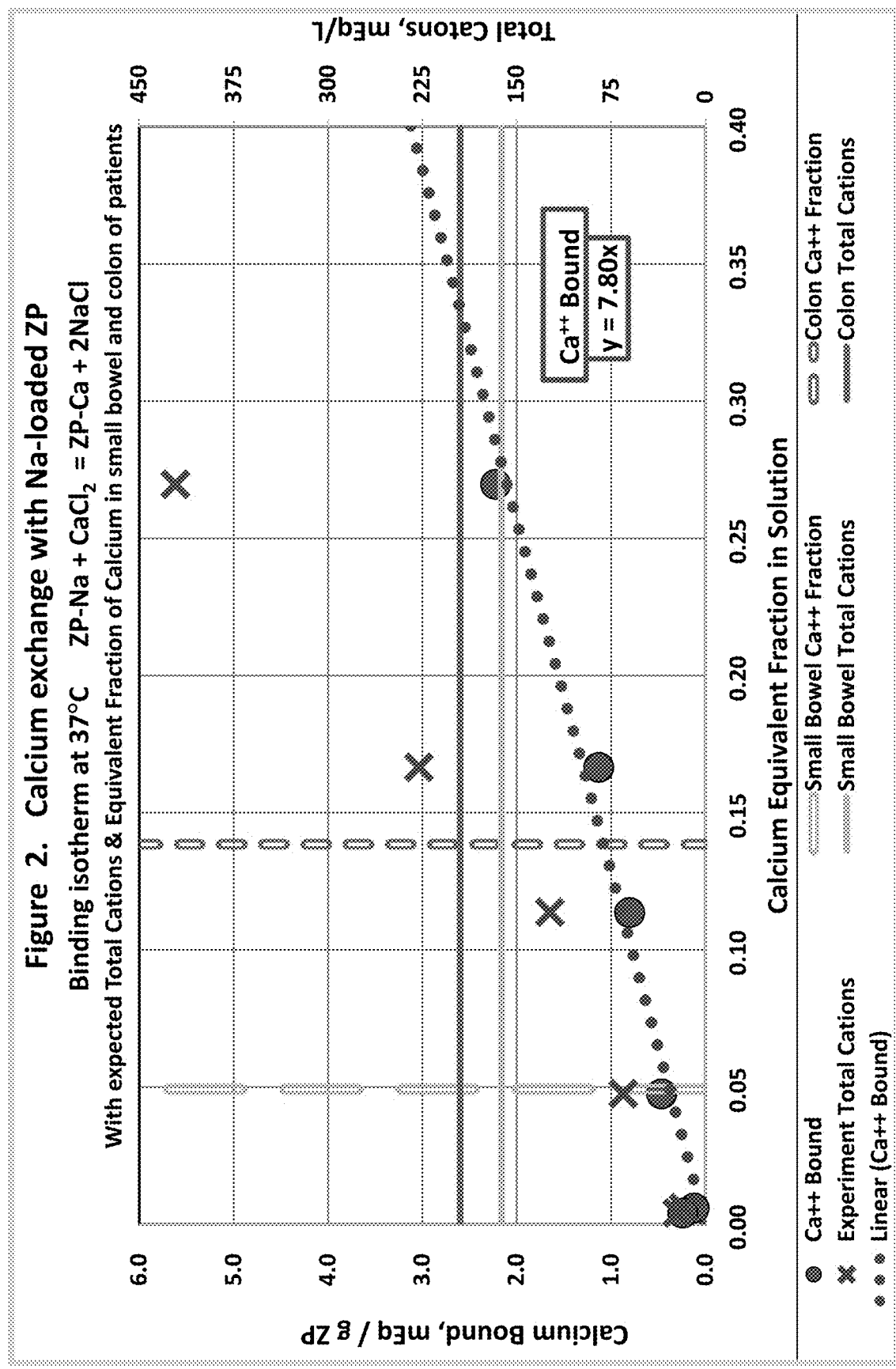

Figure 3. Magnesium exchange with Na-loaded ZP

Binding isotherm at 37°C in normal saline   Selected data   $ZP\text{-}Na + MgCl_2 = ZP\text{-}Mg + 2NaCl$
With expected Total Cations & Equivalent Fraction of Magnesium in small bowel & colon of patients

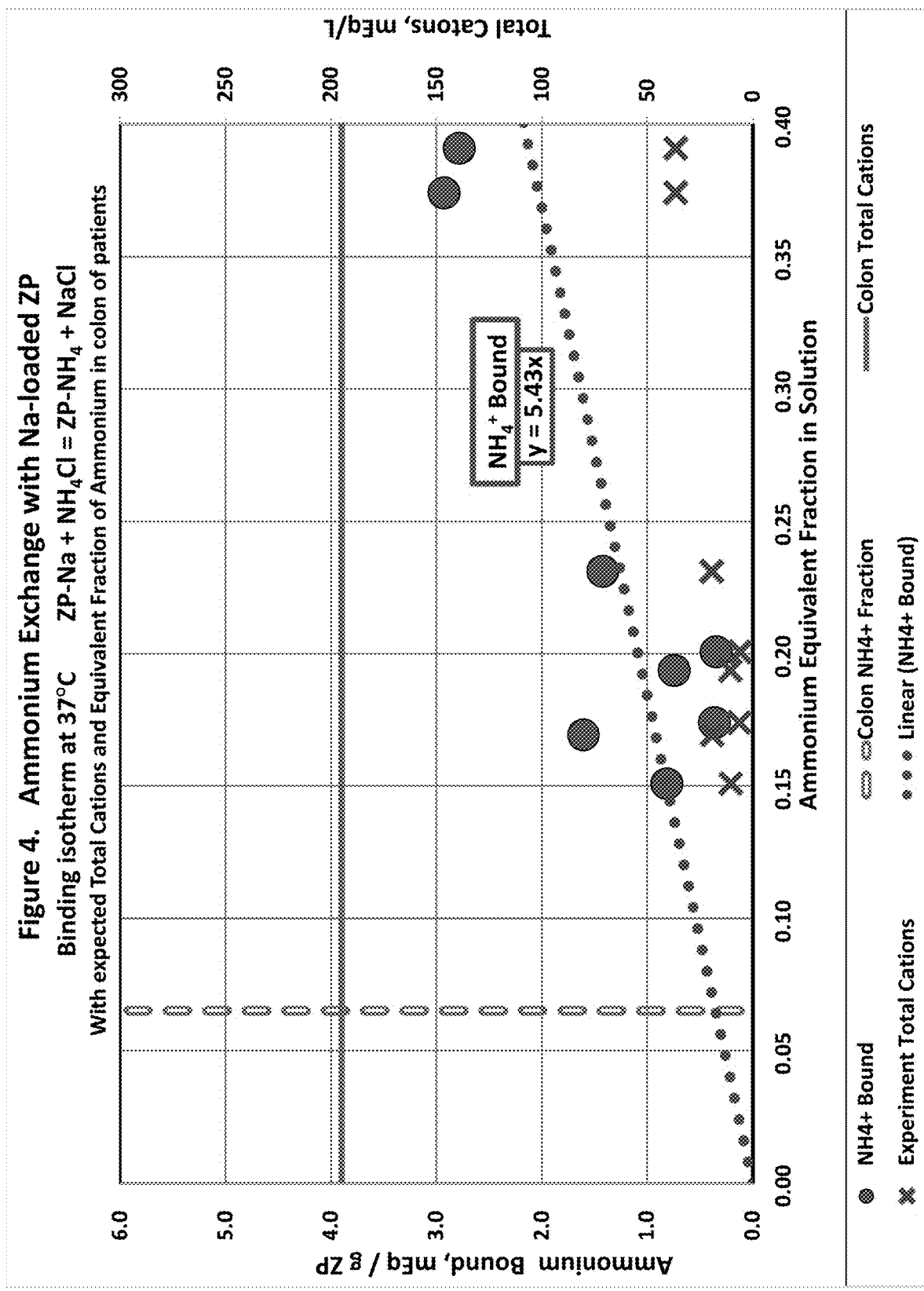
Figure 4. Ammonium Exchange with Na-loaded ZP
Binding isotherm at 37°C    ZP-Na + NH$_4$Cl = ZP-NH$_4$ + NaCl
With expected Total Cations and Equivalent Fraction of Ammonium in colon of patients

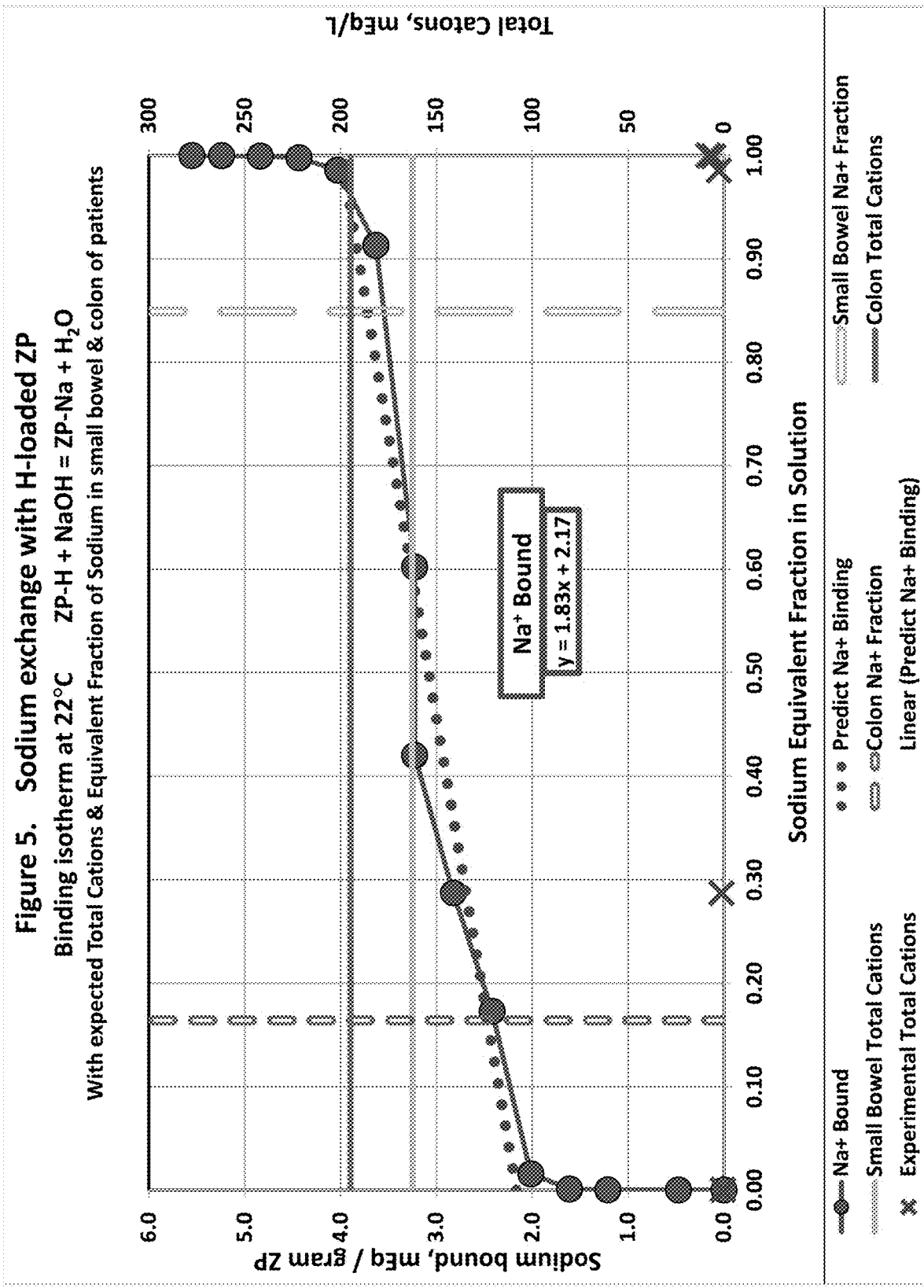

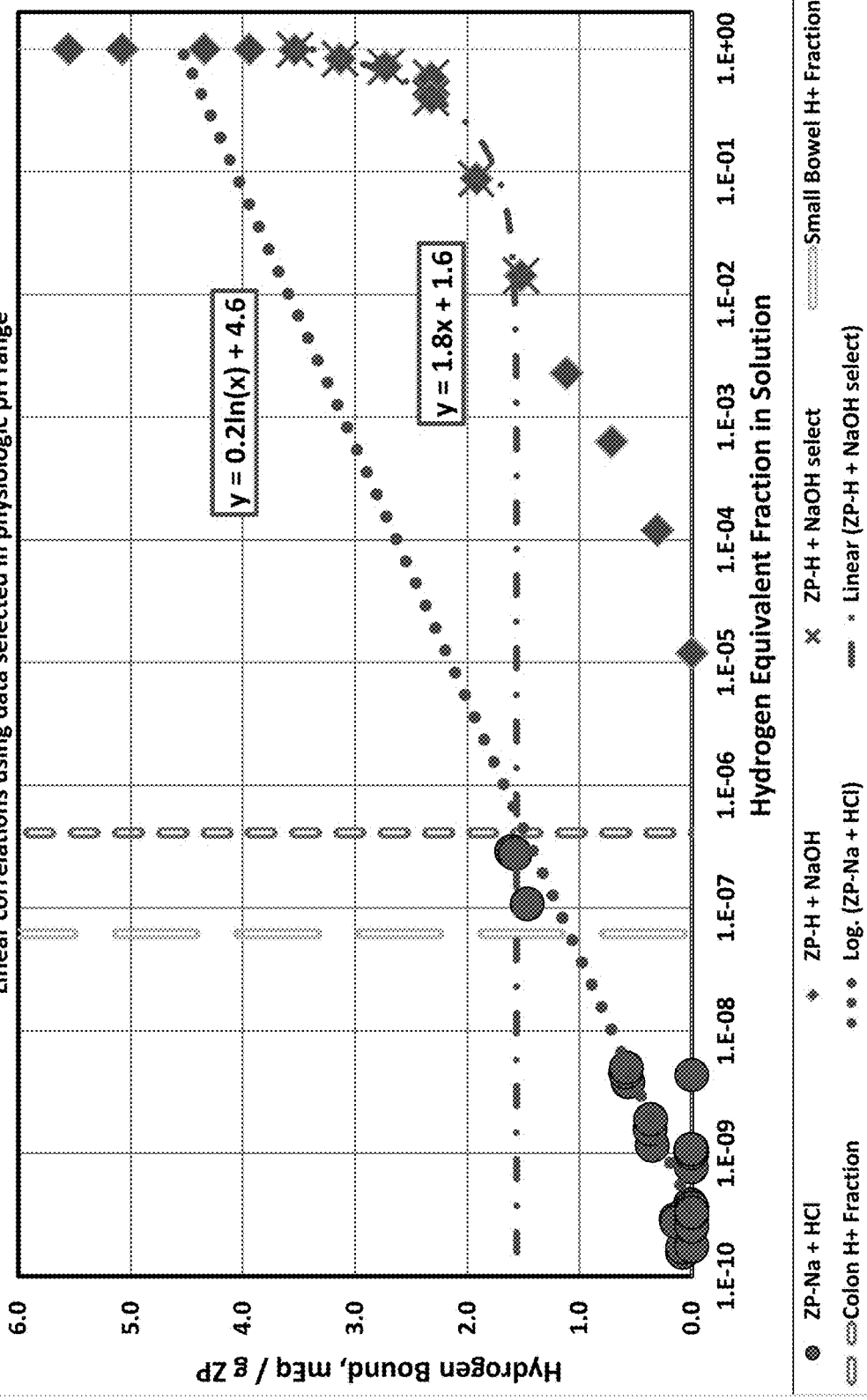

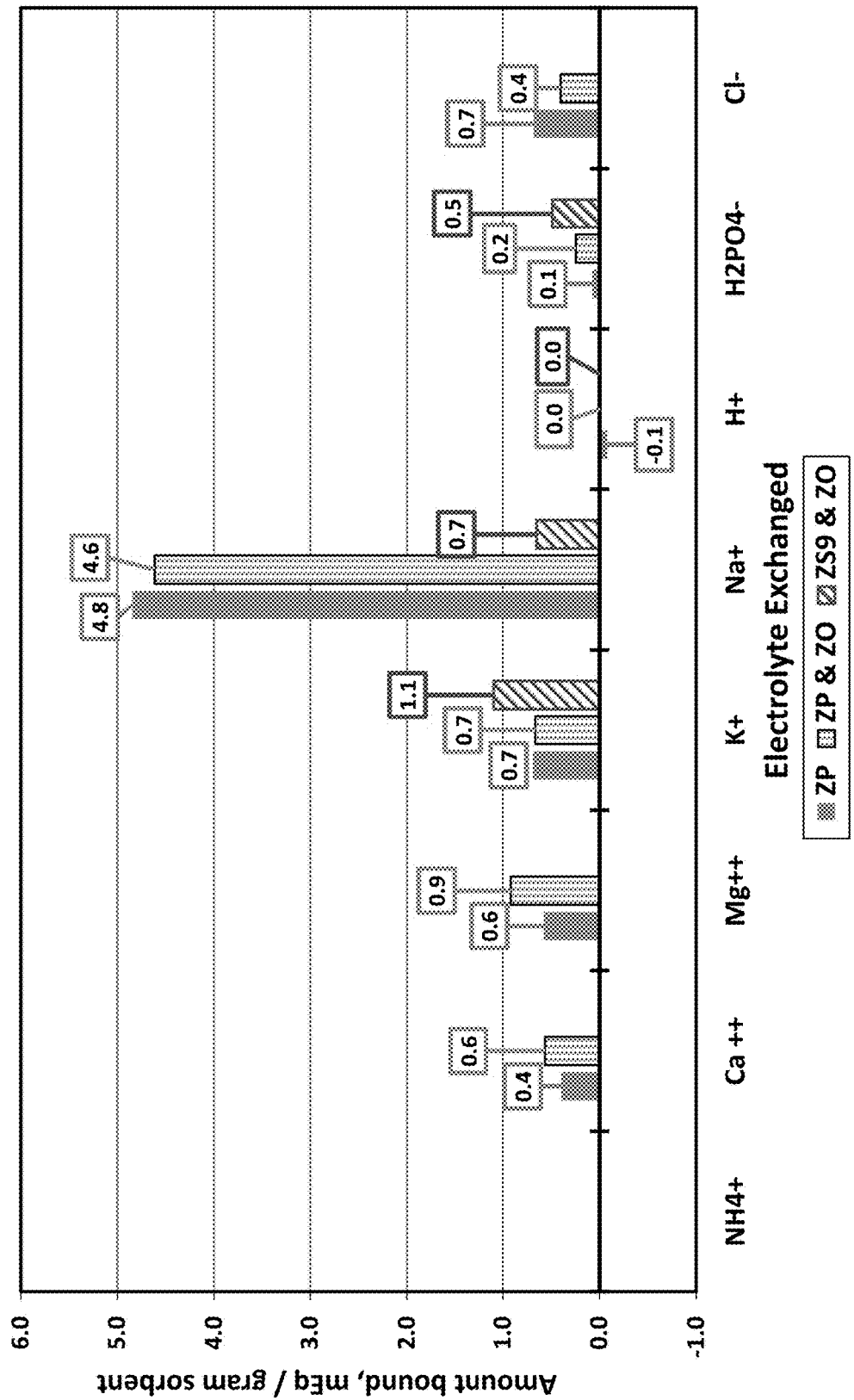
Figure 7. Electrolyte binding from SMALL BOWEL solution due to sorbents

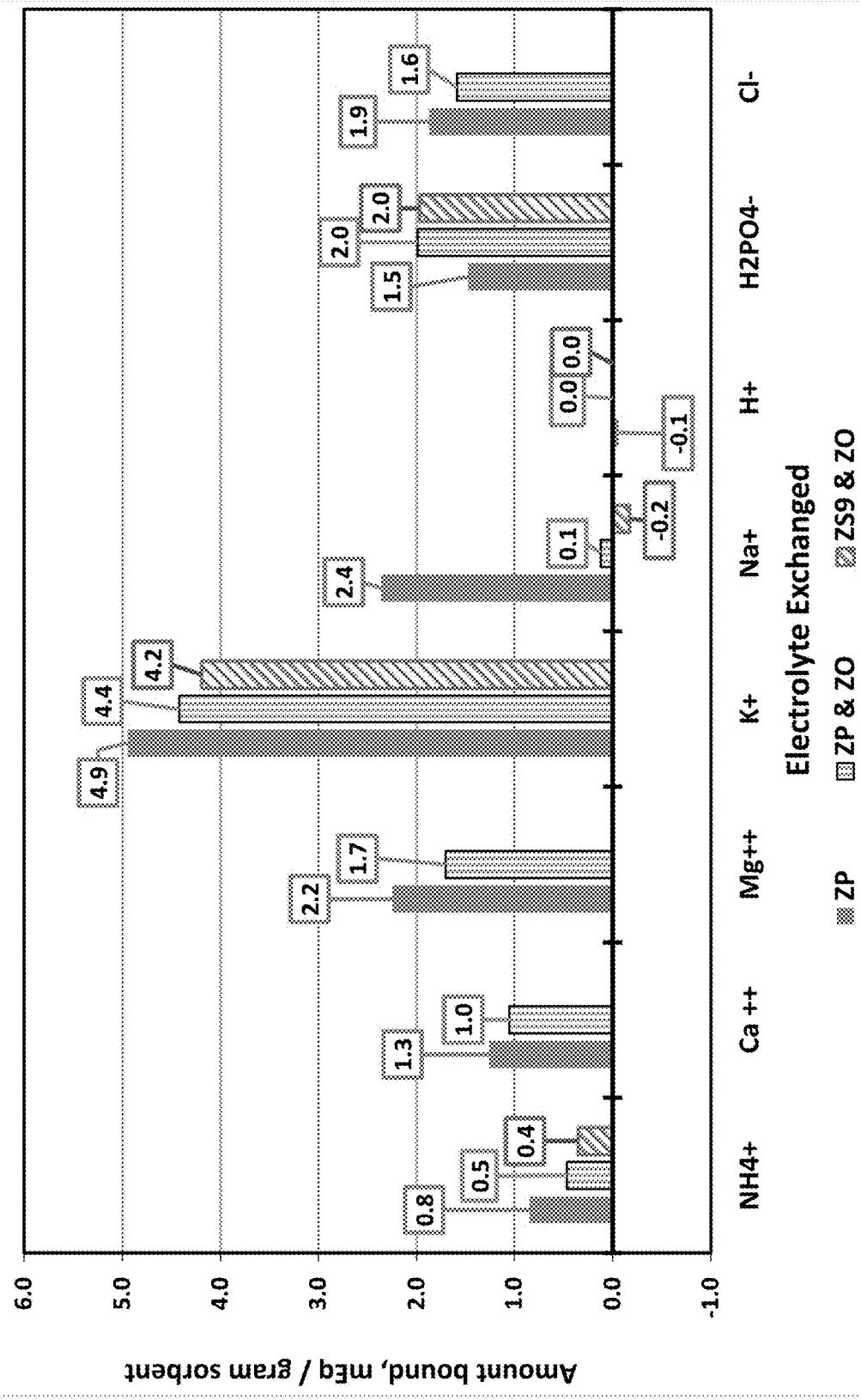
Figure 8. Electrolyte binding from COLON solution due to sorbents

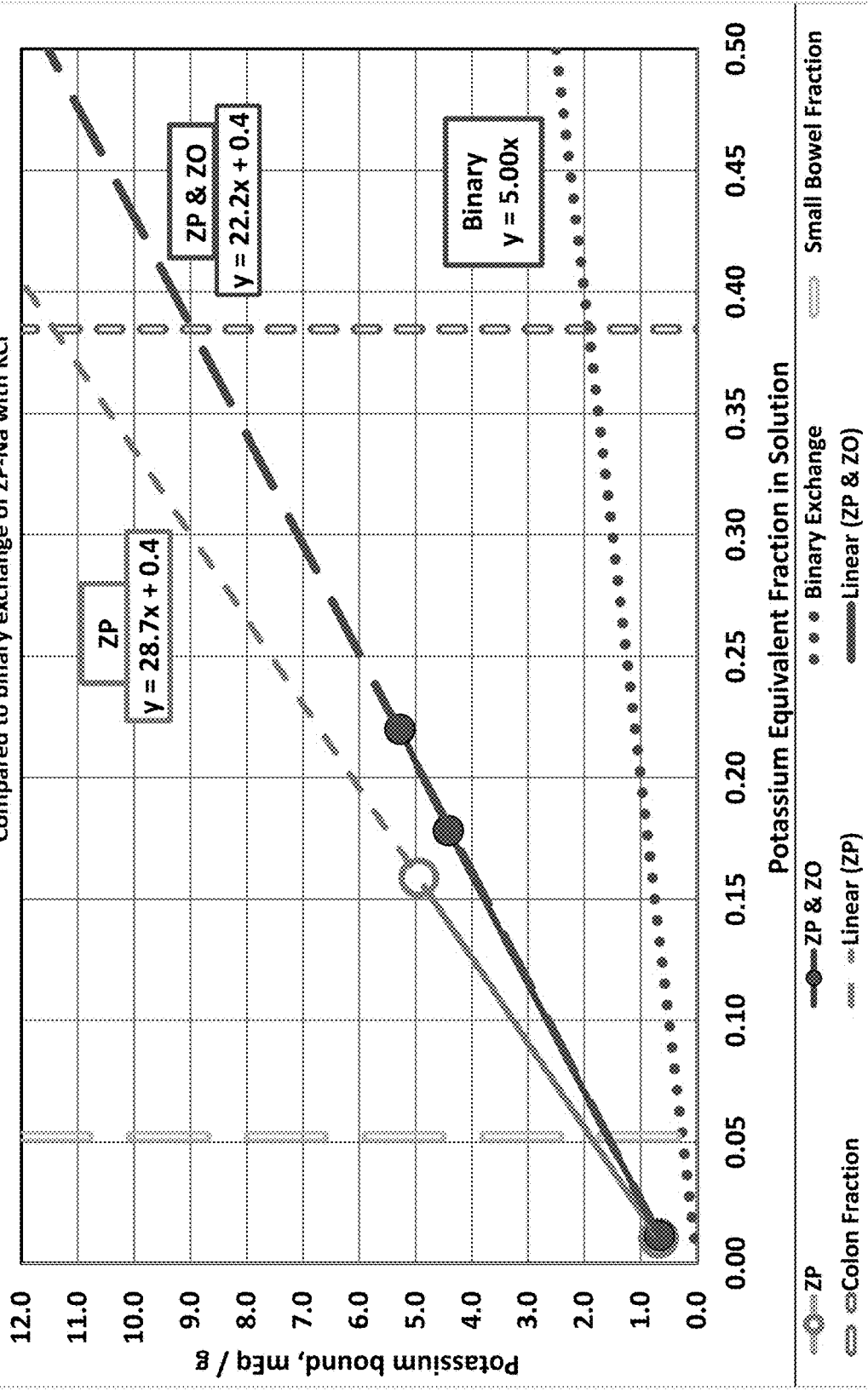
Figure 9. Potassium Binding from Physiological Solutions
Exchange with ZP or ZP & ZO
Equivalent fraction of all cations at physiologic pH
Compared to binary exchange of ZP-Na with KCl

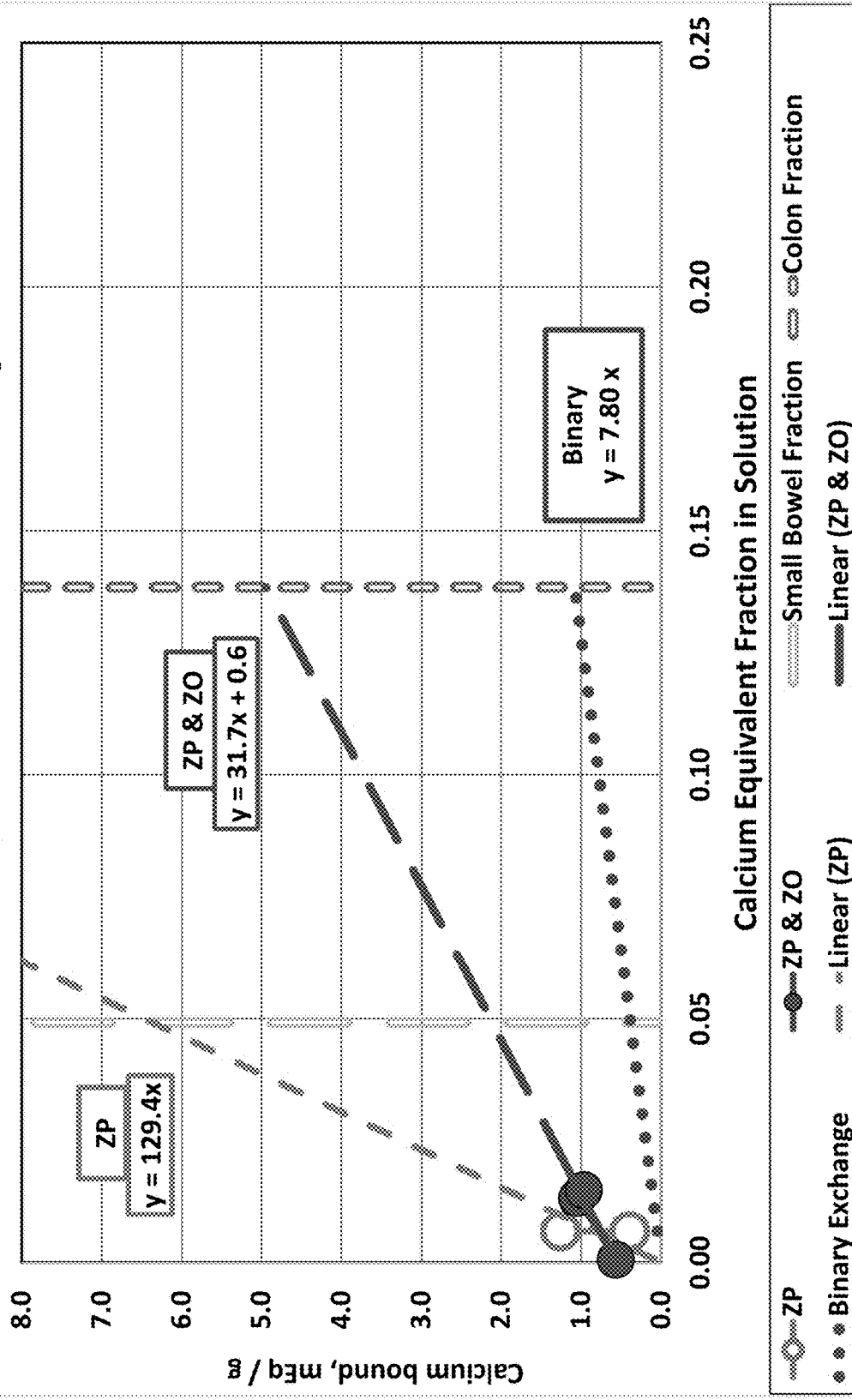
Figure 10. Calcium Binding from Physiological Solutions

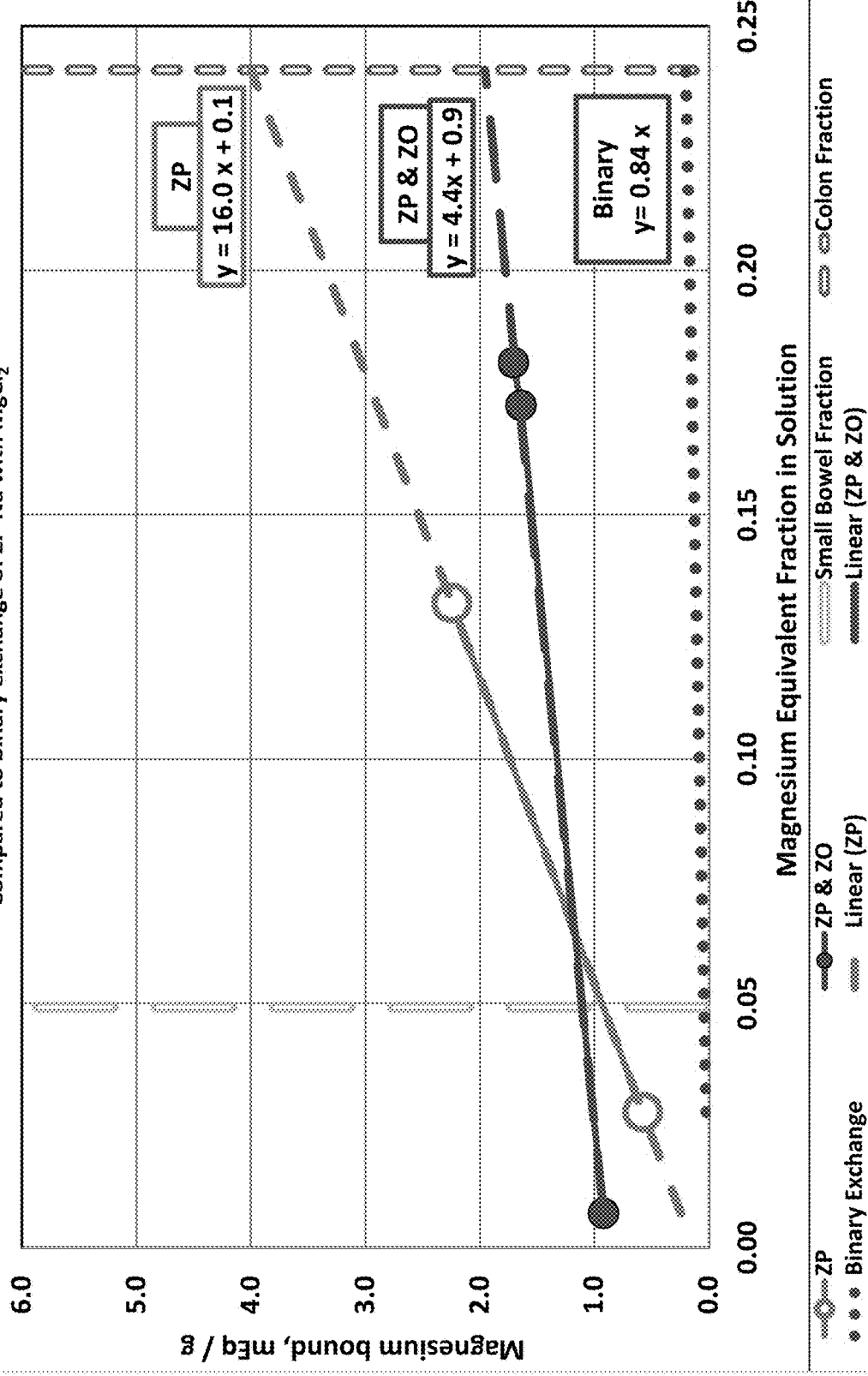

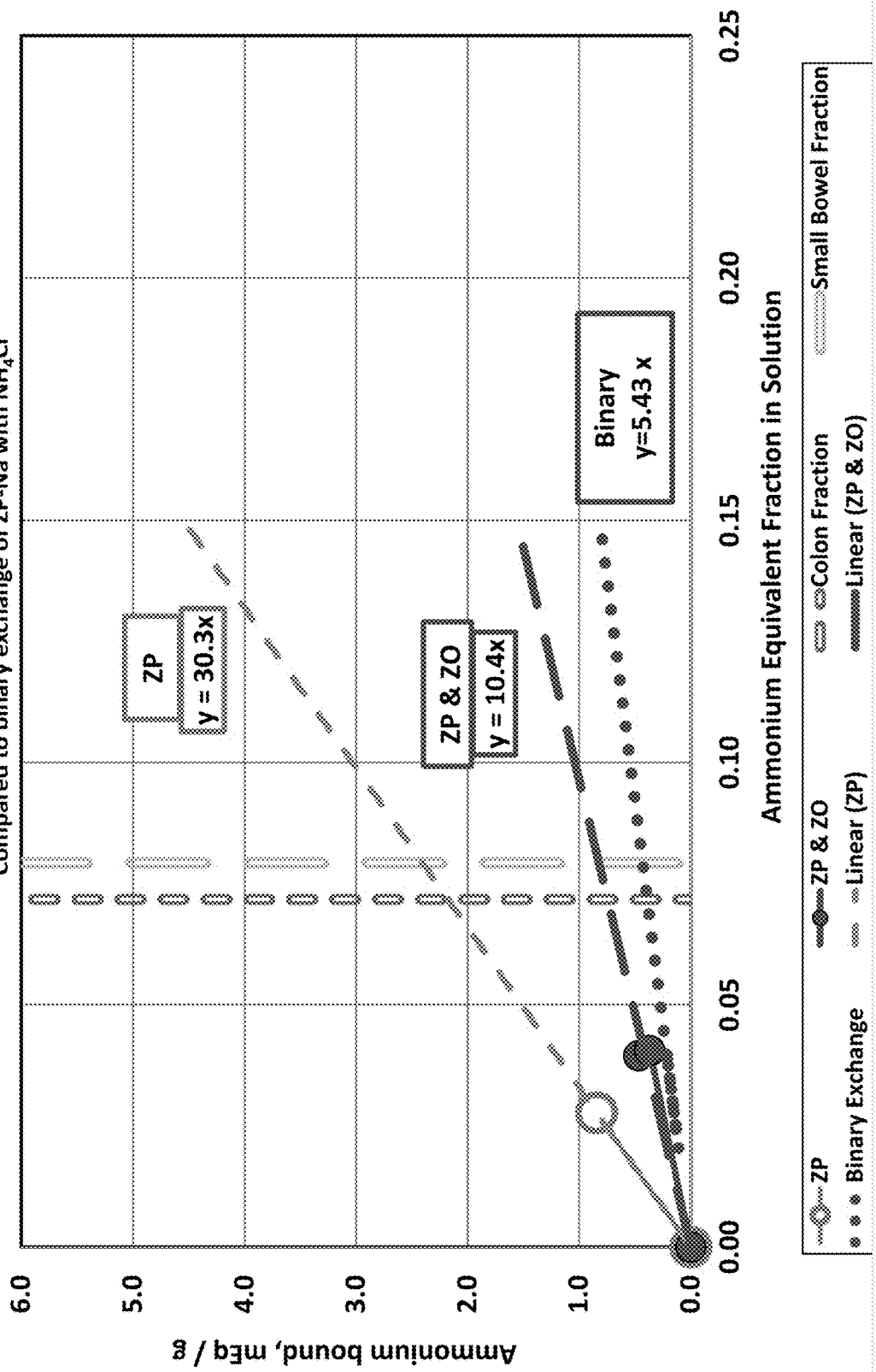
Figure 12. Ammonium Binding from Physiological Solutions

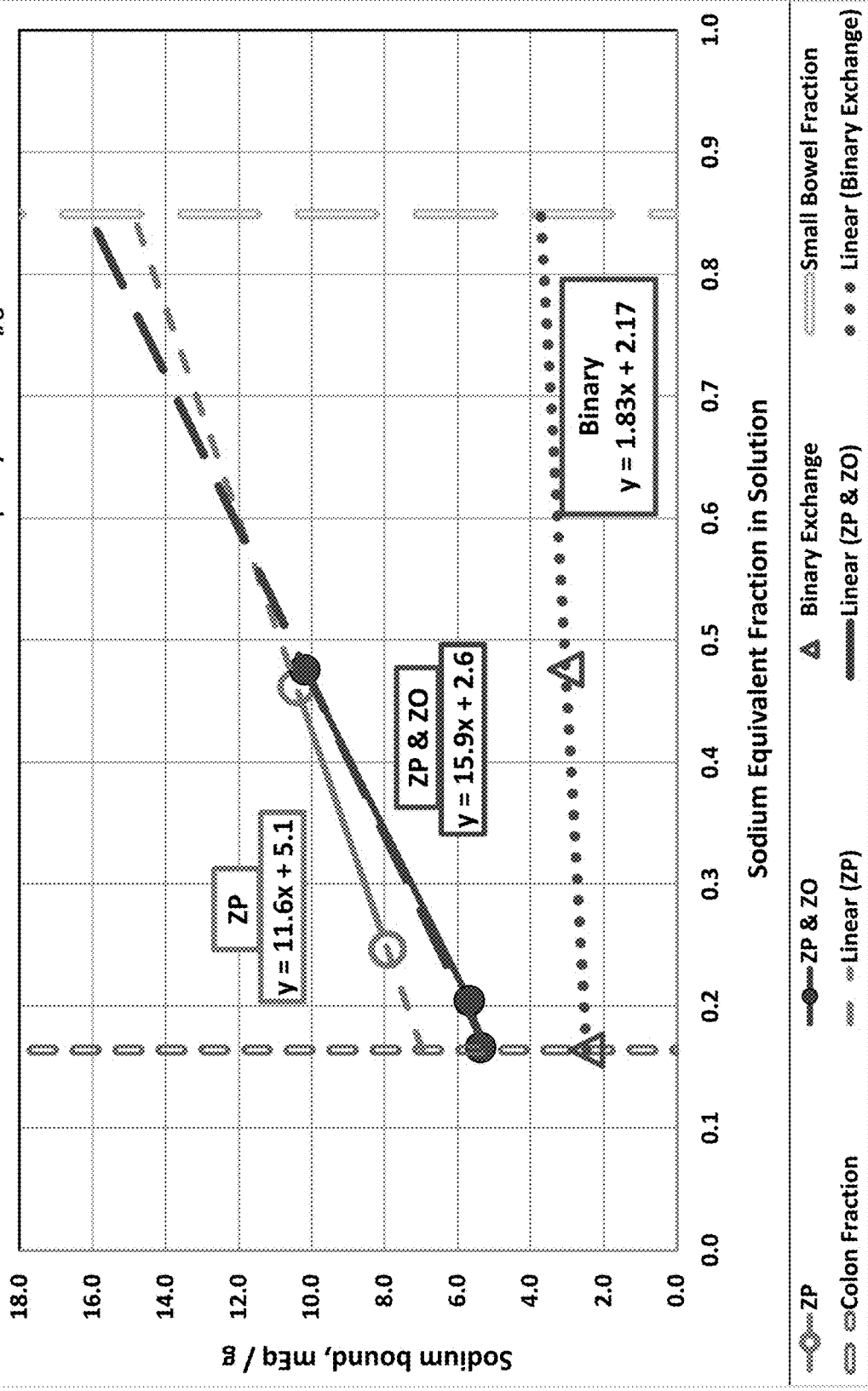

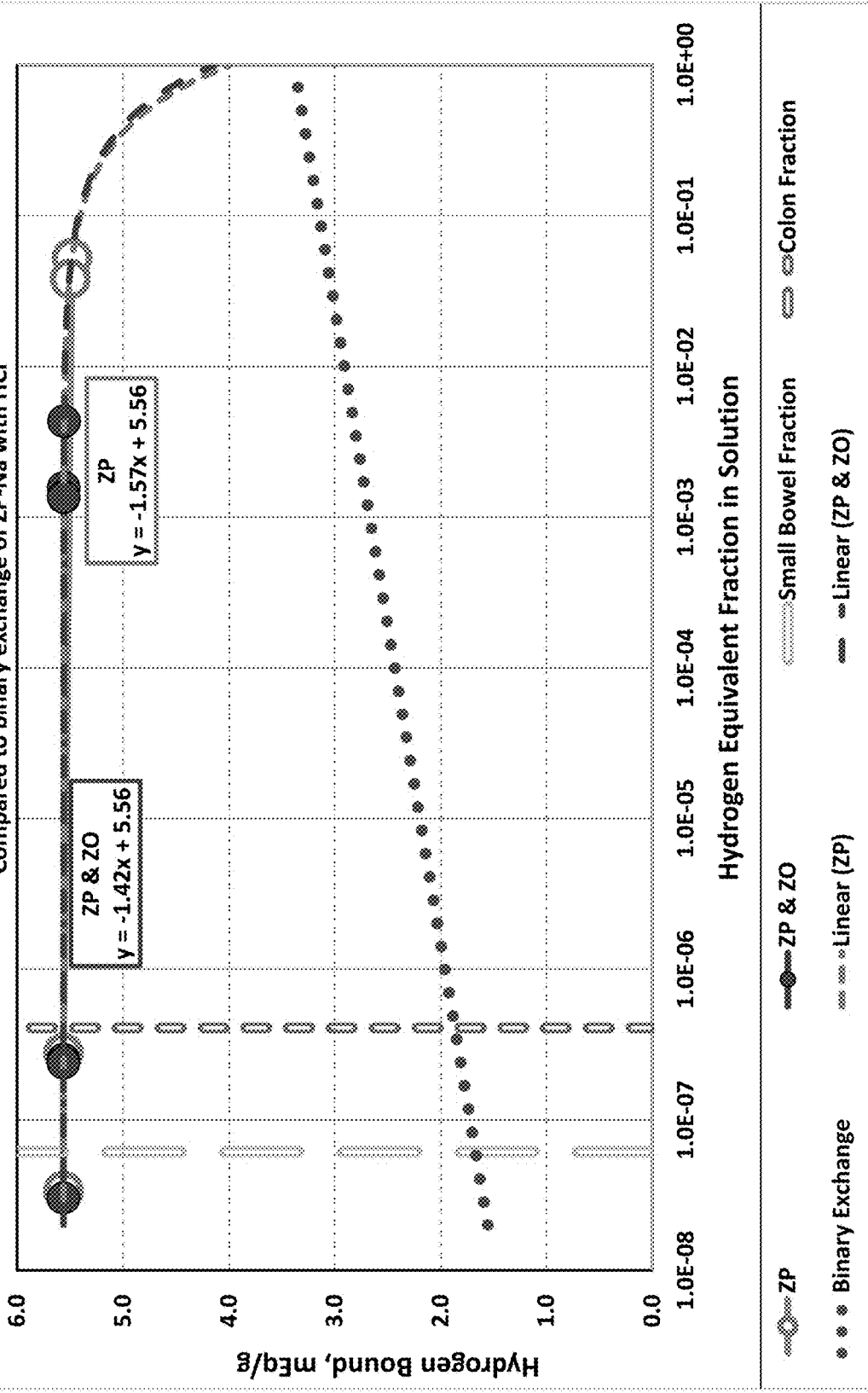

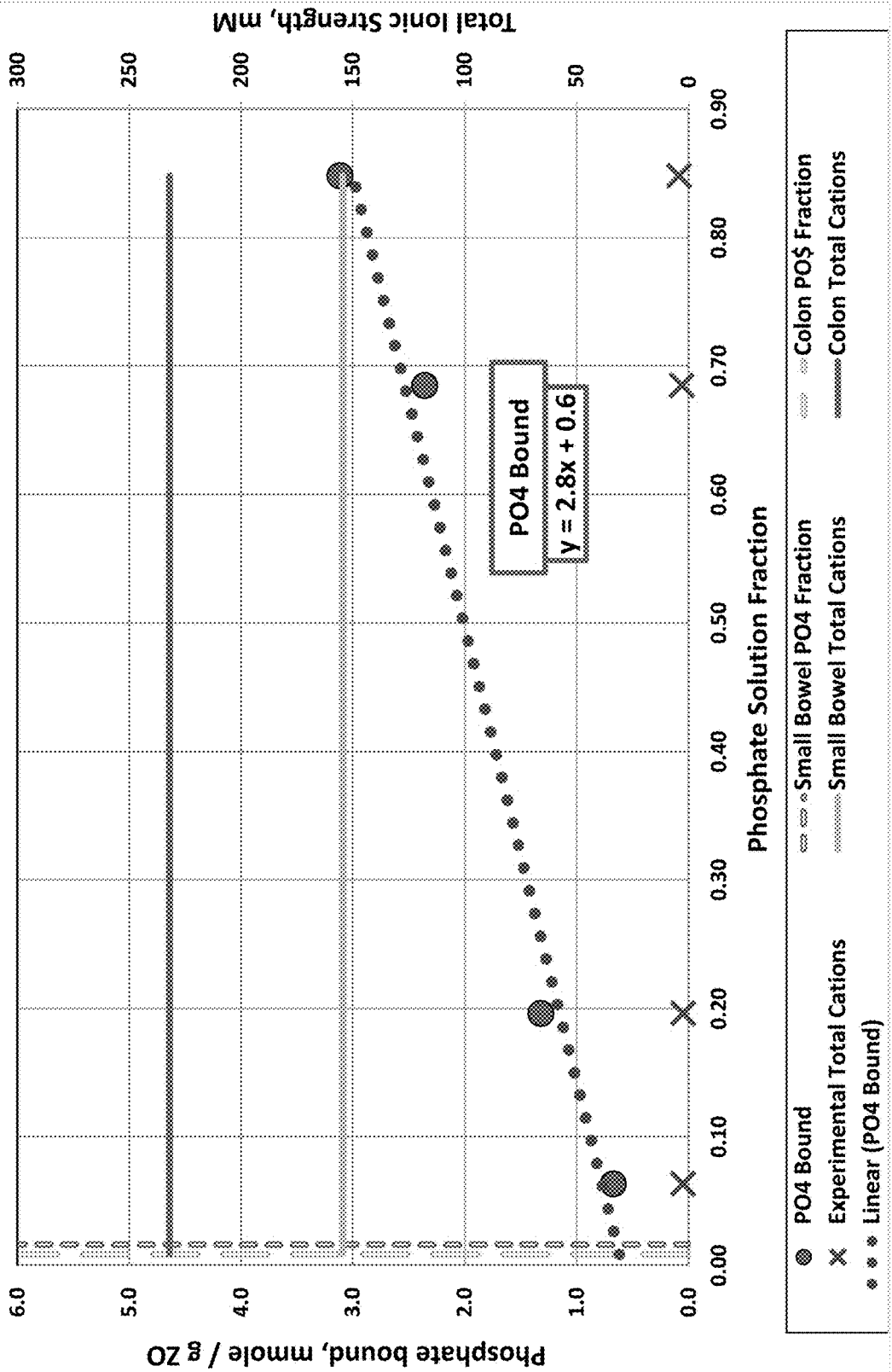
Figure 15. Phosphate Exchange with OH-loaded ZO
Binding isotherm at 37°C 1/18/2013 ZO-OH + $KH_2PO_4$ = ZO-$PO_4$ + KOH + $2H_2O$
With physiological conditions of Total Ionic Strength and Equivalent Fraction of P

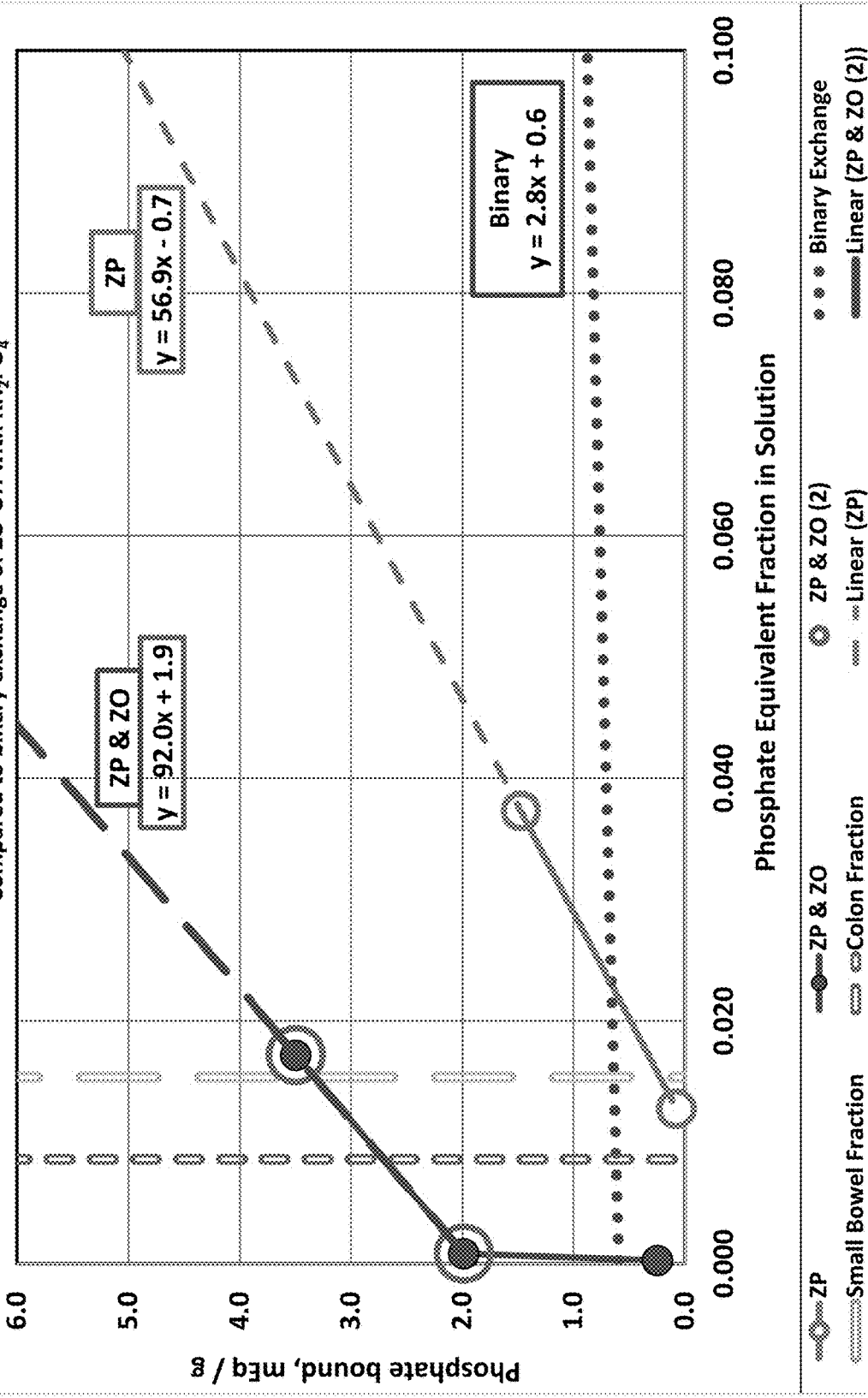

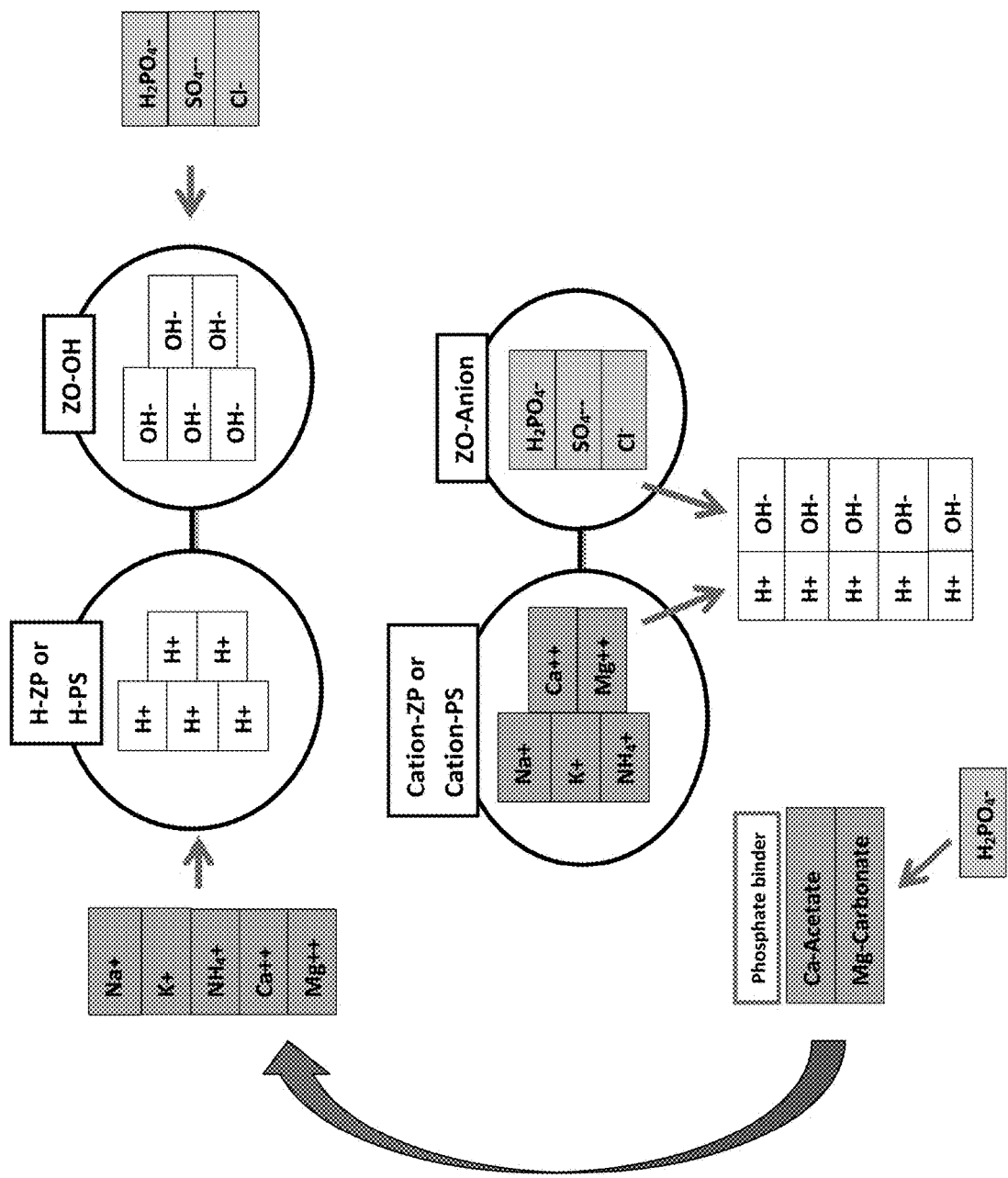
Figure 17   Hydrogen-loaded cation exchanger and hydroxide-loaded ZO exchange with cations and anion, respectively. Phosphate binder contributes to Ca and Mg bound by cation exchanger.

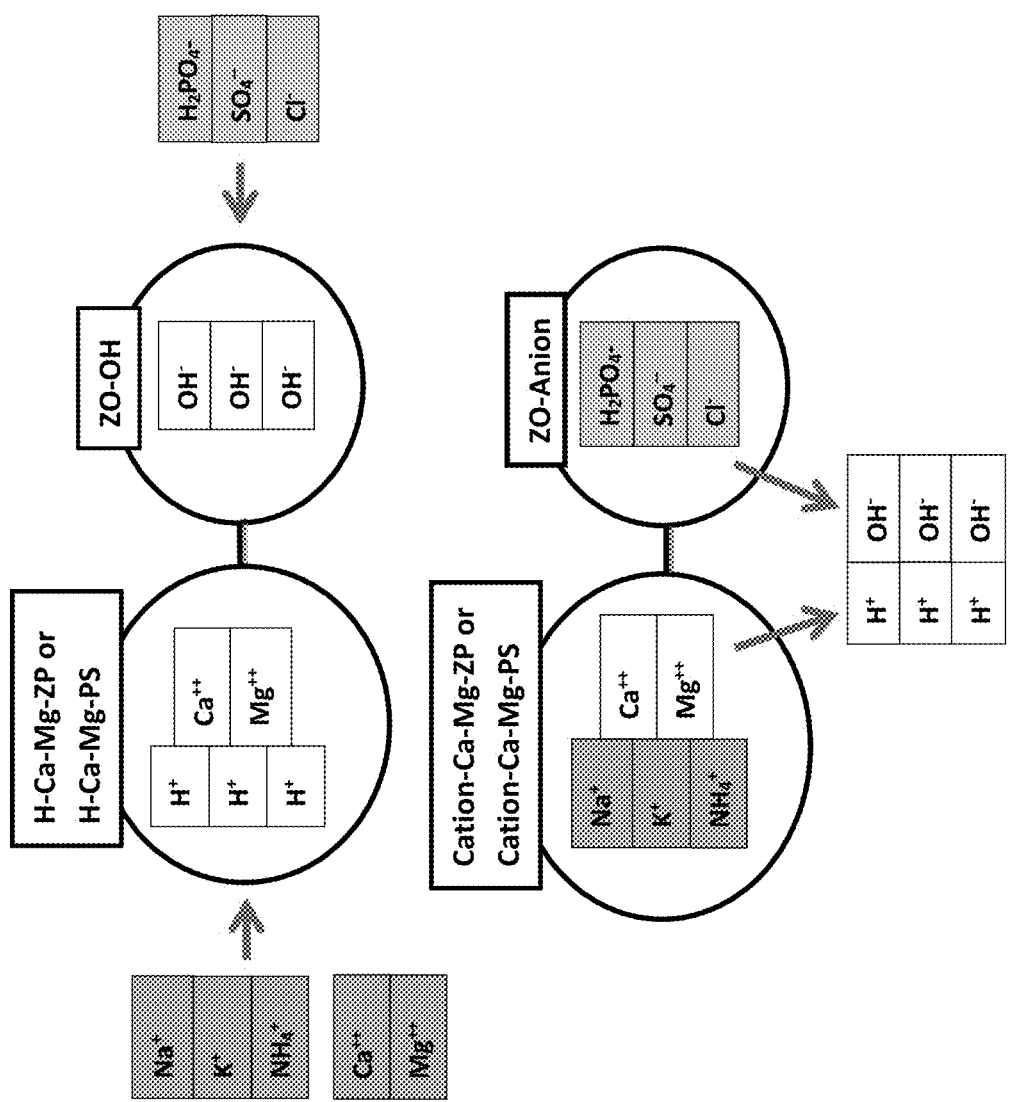
Figure 18    Hydroxide-loaded cation exchangers (ZP or PS) partially loaded with Ca and Mg plus hydroxide-loaded ZO exchanging for respective cations and anions. Calcium and magnesium in solution are mostly unaffected by sorbent.

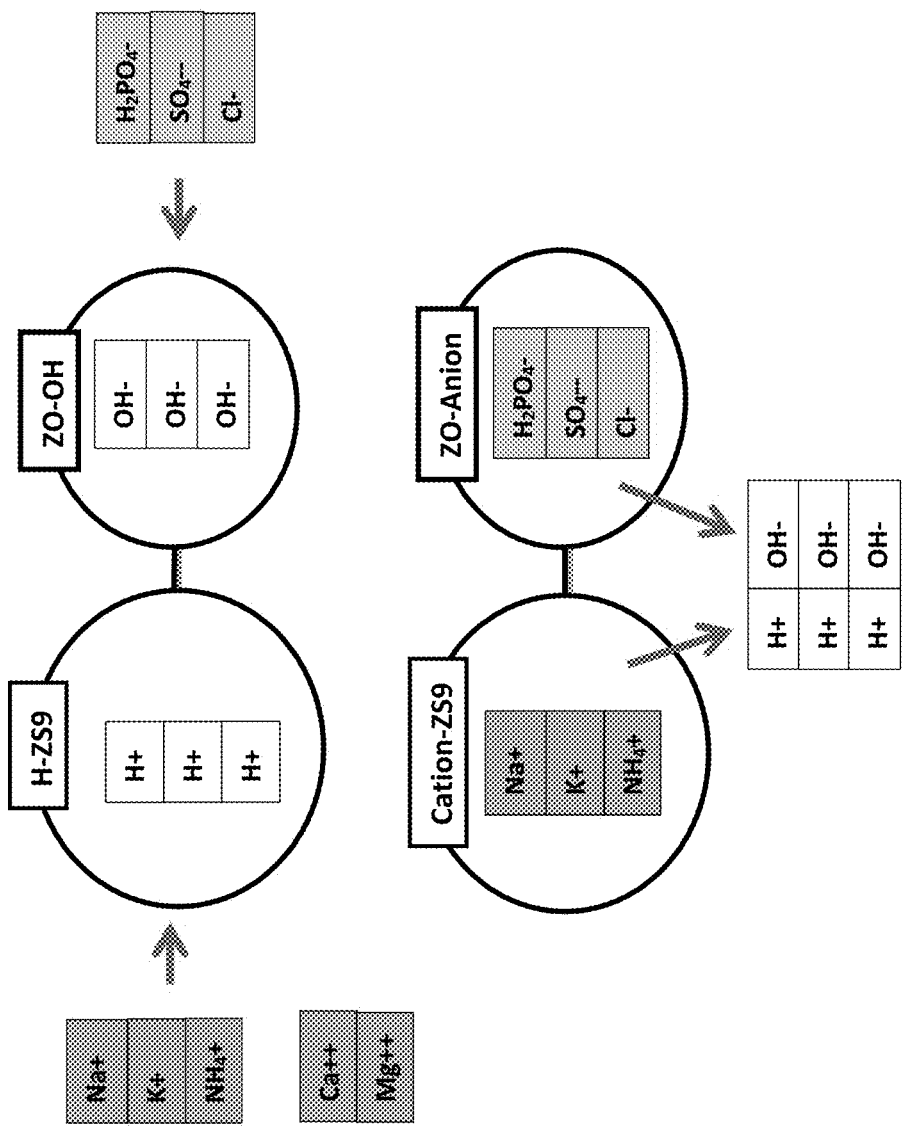
Figure 19 Hydrogen-loaded ZS9 and hydroxide-loaded ZO exchanging for cations and anions for which they have affinity. ZS9 has very low affinity for divalent cations such as $Ca^{++}$ and $Mg^{++}$.

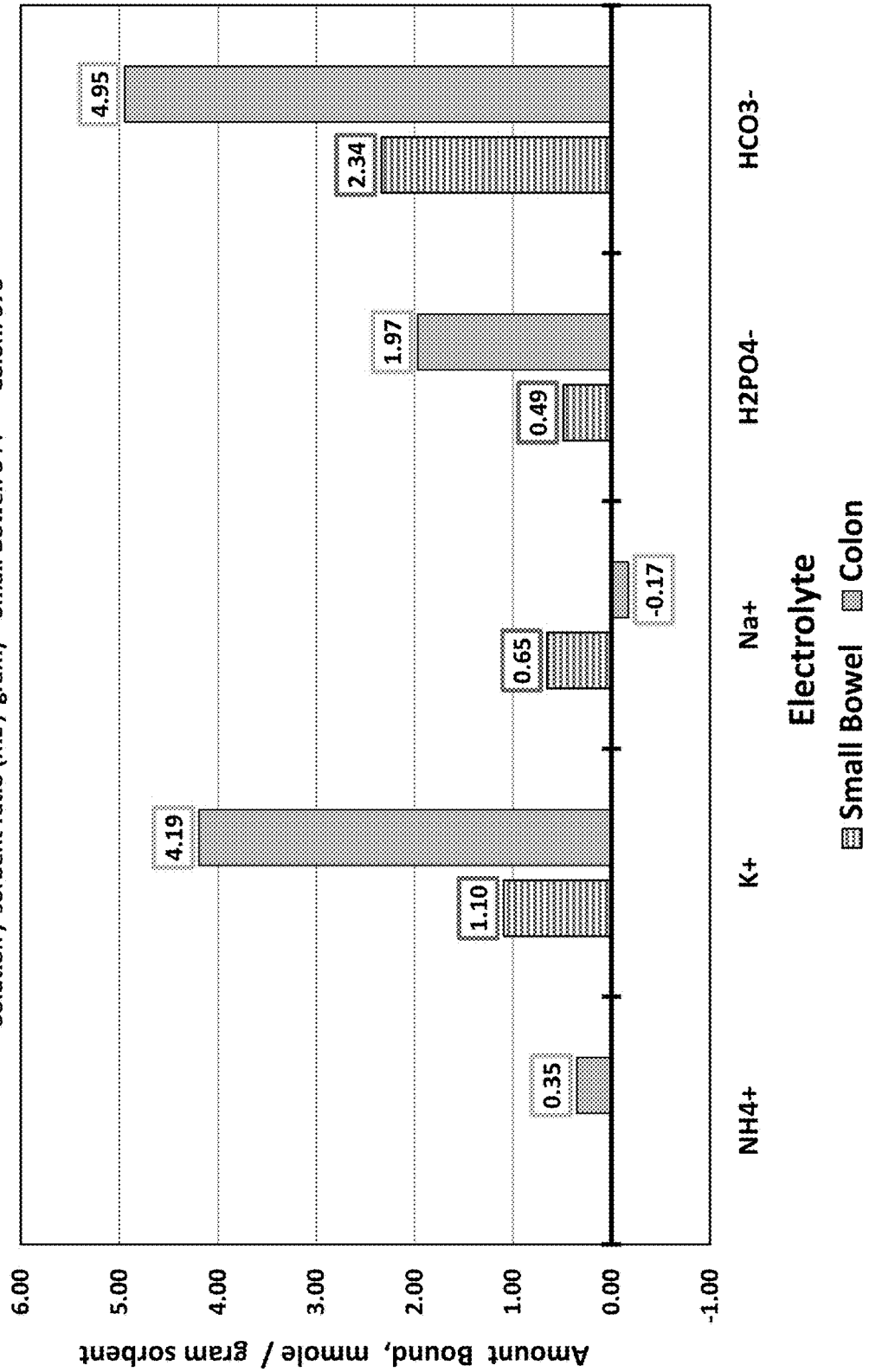

ORAL SORBENT FOR REMOVING TOXINS OF KIDNEY FAILURE COMBINING ANION AND CATION EXCHANGERS

CROSS REFERENCE

This application is a U.S. non-provisional patent application which claims the benefit of U.S. provisional patent application Ser. No. 62/529,580, filed Jul. 7, 2017, the disclosure of which is expressly incorporated by reference.

FIELD

This disclosure includes oral sorbent compound that binds the small and charged toxins.

BACKGROUND

When kidneys fail, there are numerous toxins that accumulate in the blood. Many of these toxins are small molecules with positive or negative charge such as potassium, sodium, hydrogen, ammonium (generated from urea in the gut) and phosphate. Other toxins are uncharged organic molecules of small to large molecular weight (100-3,000 MW). Many of the small molecular weight and charged toxins affecting patients with kidney failure come into the patient through ingested food. Others, such as ammonium, are generated by passage of urea across the intestinal membranes and catalysis by bacterial urease within the gastrointestinal (GI) tract.

Organic toxins do penetrate the intestinal membranes somewhat and some are generated within the colon.

Currently the sodium form of sodium-loaded polystyrene sulfonate (PS) (Na-PS or Kayexalate® marketed by Sanofi) is taken as an oral powder in suspension for removal of potassium from the gut and from patients with high serum potassium levels. Na-PS was first approved by FDA for market in the 1960s. See FLINN R B, MERRILL J P, WELZANT W R. Treatment of the oliguric patient with a new sodium-exchange resin and sorbitol; a preliminary report. N Engl J Med. 1961 Jan. 19; 264:111-5 and Mahoney B A, Smith W A, Lo D S, Tsoi K, Tonelli M, Clase C M. Emergency interventions for hyperkalaemia. Cochrane Database Syst Rev. 2005 Apr. 18; (2):CD003235. However sodium release is a problem with this powder, especially if used for a long period. See Kovesdy C P. Management of hyperkalaemia in chronic kidney disease (CKD). Nat Rev Nephrol. 2014 Sep. 16. Hydrogen-loaded PS (H-PS) has also been tested in animal studies and shown to remove small amounts of potassium from animals, without adverse consequences but this causes a loss of serum sodium and acidosis (decrease in serum bicarbonate). See T. S. DANOWSKI, L. GREENMAN, F. M. MATEER, W. B. PARSONS, F. A. WEIGAND, H. MERMELSTEIN, AND J. H. PETERS. CARBOXYLIC CATION EXCHANGE RESIN EFFECTS IN DOGS. Journal of Clinical Investigation, p. 984-994, 1951. In Europe PS is also available in the calcium form (Ca-PS) and is marketed by Fresenius Medical Care (FMC) as Sorbisterit and is also available in Japan as Argamate (jelly type) and Kalimate (powder type). See Tomino Y, Yamazaki T, Shou I, Tsuge T, Satake K, Takeda Y, Ohtani A, Nishitani T, Kurusu A, Hamada C, Horikoshi S, Maeda K, Tanaka Y, Fukuda H, Wakabayashi M, Seto T. Dose-response to a jelly preparation of calcium polystyrene sulfonate in patients with hyperkalemia—changes in serum potassium levels with or without a RAAS inhibitor. Clin Nephrol. 2007 December; 68 (6): 379-85. This formulation may increase serum calcium levels and has a lower capacity for potassium than the sodium form due to the preference of PS for divalent cations. Fortunately the concentration of these exchangeable divalent cations in the gut is relatively low, so only about 25-50% of the capacity of the PS will be taken up by the divalent cations.

Working with Union Carbide and their joint-venture UOP, Inc. over many years, Dr. Ash advised these companies of the importance of finding cation exchangers that would be specific for binding monovalent cations and would not bind divalent cations. Such sorbents would have higher capacity for binding potassium and ammonium (from urea) during therapy of patients with kidney failure, whether used as oral sorbents or as a column used to regenerate dialysate during extracorporeal dialysis therapies. The first generation of compounds developed by Union Carbide were synthetic zeolites, which had the ability to exchange calcium or magnesium for the monovalent cations. However, the partial solubility of these compounds resulted in release of aluminum and silica, and this limited their safety in use either as oral sorbents or as dialysate regenerating compounds. After many years of research, UOP, Inc. developed zirconium cyclosilicate (ZS9), a crystalline compound with pores that are designed to optimally interact with charges on monovalent cations but sub-optimal in interactions with divalent cations (U.S. Pat. Nos. 8,802,152 and 8,808,750). ZS9 is selective in its binding for monovalent cations (potassium, sodium, hydrogen and ammonium) and thus does not become loaded with divalent cations (such as calcium and magnesium).

In sodium-hydrogen loaded form zirconium cyclosilicate has been shown to be an effective binder for potassium and ammonium in the gut (U.S. Pat. Nos. 8.802,152 and 8,808, 750). Clinical trials have shown that this product can effectively remove potassium from patients when taken orally as an intestinal sorbent, decreasing the serum potassium levels by about 1 mEq/L in 48 hours, for patients with chronic kidney disease (CKD) who have high potassium levels. See Stephen R. Ash, Bhupinder Singh, Philip T. Lavin, Fiona Stavros, Henrik S. Rasmussen. Safety and Efficacy of ZS-9, a Novel Selective Cation Trap, for Treatment of Hyperkalemia in CKD Patients. Presented at ASN High Impact Abstracts Session, Nov. 11, 2013. Additionally the clinical trials showed that there was a small but significant decrease in serum urea nitrogen (BUN) level, apparently due to binding of ammonium in the gut. Because the crystal is partially loaded with hydrogen, and because there are buffers like bicarbonate in the gut, the exchange of potassium and ammonium is principally for hydrogen, and there appears to be little or no net transfer of sodium to the patient. See Ash, Stephen R., Singh, Bhupinder; Lavin, Philip; Stavros, Fiona; Rasmussen, Henrik. Safety and Efficacy of ZS-9, a Novel, Selective Potassium Trap: Results of a Phase 2 Study of the Treatment of Hyperkalemia in Patients with CKD. Accepted for publication in Kidney International, September 2014. However, ZS9 does not remove any excess sodium from the patient. For end stage renal disease (ESRD) patients with fluid overload, a system to remove sodium would be very helpful and almost all ESRD patients need a phosphate binder also.

One clinical finding in our studies of ZS9 was that patients tolerated ingestion of this inorganic sorbent very well. Ten gram doses of the very fine powder were mixed in small amounts of water and drunk from a glass. As opposed ingestion of resins such as Na-PS, there were no complaints of grittiness, malodor or poor taste. Patients generally agreed that ingestion of the powder was more comfortable than taking a large number of pre-formed tablets. This advantage also applies to other inorganic ion exchangers such as ZP and ZO (discussed below).

BRIEF DESCRIPTION OF THE DRAWINGS

The above-mentioned and other features of this disclosure, and the manner of attaining them, will become more apparent and the disclosure itself will be better understood by reference to the following description of embodiments of the disclosure taken in conjunction with the accompanying drawings, wherein:

FIG. 1 shows potassium in solution equivalent fraction exchange with sodium loaded zirconium phosphate.

FIG. 2 shows calcium in solution equivalent fraction exchange with sodium loaded zirconium phosphate.

FIG. 3 shows magnesium in solution equivalent fraction exchange with sodium loaded zirconium phosphate.

FIG. 4 shows ammonium in solution equivalent fraction exchange with sodium loaded zirconium phosphate.

FIG. 5 shows sodium in solution equivalent fraction exchange with hydrogen loaded zirconium phosphate.

FIG. 6 shows hydrogen binding isotherms for zirconium phosphate.

FIG. 7 shows electrolyte exchange of small bowel simulated solution with various sorbents and combinations of sorbents (ZP, ZP and ZO, and ZS9 and ZO).

FIG. 8 shows electrolyte exchange of colon simulated solution with various sorbents and combinations of sorbents (ZP, ZP and ZO, and ZS9 and ZO).

FIG. 9 shows potassium exchange in physiological solutions with hydrogen loaded zirconium phosphate or hydrogen loaded zirconium phosphate in combination with hydroxide loaded zirconium oxide.

FIG. 10 shows calcium exchange in physiological solutions with hydrogen loaded zirconium phosphate or hydrogen loaded zirconium phosphate in combination with hydroxide loaded zirconium oxide.

FIG. 11 shows magnesium exchange in physiological solutions with hydrogen loaded zirconium phosphate or hydrogen loaded zirconium phosphate in combination with hydroxide loaded zirconium oxide.

FIG. 12 shows ammonium exchange in physiological solutions with hydrogen loaded zirconium phosphate or hydrogen loaded zirconium phosphate in combination with hydroxide loaded zirconium oxide.

FIG. 13 shows sodium exchange in physiological solutions with hydrogen loaded zirconium phosphate or hydrogen loaded zirconium phosphate in combination with hydroxide loaded zirconium oxide.

FIG. 14 shows hydrogen exchange in physiological solutions with hydrogen loaded zirconium phosphate or hydrogen loaded zirconium phosphate in combination with hydroxide loaded zirconium oxide.

FIG. 15 shows phosphate exchange in physiological solutions with hydroxide loaded zirconium oxide.

FIG. 16 shows phosphate exchange in physiological solutions with hydrogen loaded zirconium phosphate or hydrogen loaded zirconium phosphate in combination with hydroxide loaded zirconium oxide.

FIG. 17 illustrates a scheme of operation of the mixed ion exchanger sorbent, using nonspecific cation exchangers such as H-PS or H-ZP, a nonspecific anion exchanger such as OH-ZO, and providing calcium and magnesium salts such as Ca-Acetate/Mg-Carbonate to offset binding of divalent cations.

FIG. 18 illustrates a scheme of operation of the mixed ion exchanger sorbent, using nonspecific cation exchangers such as H-PS or H-ZP that are partially pre-loaded with calcium and magnesium and a nonspecific anion exchanger such as OH-ZO.

FIG. 19 illustrates a scheme of operation of the mixed ion exchanger sorbent using hydrogen-loaded zirconium cyclosilicate (a cation exchanger that is specific for monovalent cations) and the nonspecific anion exchanger OH-ZO.

FIG. 20 electrolyte exchange of physiologic solutions with a combination of sorbents (ZS9 and ZO). Data for this combination is repeated in FIGS. 7 and 8, for comparison to other sorbent combinations.

For FIGS. 17, 18, and 19, corresponding reference characters indicate corresponding parts throughout the several views. Although the drawings represent embodiments of the present disclosure, the drawings are not necessarily to scale and certain features may be exaggerated in order to better illustrate and explain the present disclosure.

SUMMARY

An oral sorbent compound that binds the small and charged toxins of kidney failure could be highly effective in preventing their rise in concentration in blood during kidney failure, and removing toxins such as urea when they have accumulated in the blood. Such an oral sorbent could avoid the need for dialysis in many patients altogether, and delay it in other patients. Further, because of removal of nitrogen and other toxins by an oral sorbent, patients could continue to eat an unrestricted diet in the later stages of kidney failure, with as much meat, fruit, milk products and salt as they wish. This would maintain the patients in better nutritional health as they pass through the later stages of kidney diseases towards kidney failure.

The equipment for hemodialysis and peritoneal dialysis could be greatly simplified if its only function was to remove organic toxins. For example, the dialysate could be regenerated by perfusion through a charcoal column alone and used for long periods, rather than passing through a dialyzer and down the drain. An effective oral sorbent for charged uremic toxins would allow such simplification to occur in dialysis machinery that even wearable or implantable dialysis machines are conceivable.

For removal of charged molecules from water, the mixed bed ion exchanger has been remarkably effective. This is a combination of a cation exchanger that is hydrogen-loaded with an anion exchanger that is hydroxide-loaded (similar to the systems shown in FIGS. 17-19). When a cation presents in association with an anion the cation is removed in exchange for hydrogen and the anion removed in exchange for hydroxide. The hydrogen and hydroxide combine to form water. Thus there is no persisting concentration of the counter-ion to further diminish absorption of the various charged molecules. As a result mixed bed ion exchangers have a very high capacity for removal of all ions. Most laboratories that need to have highly purified water use the mixed-bed ion exchanger column to purify water, and the column reduces the concentration of ionic species to nearly zero (resulting in electrical resistance over 2 M ohm). We are proposing using hydrogen-loaded cation exchangers and hydroxide-loaded anion exchangers in combination as an orally ingested mixture to remove various charged toxins of kidney failure within the GI tract.

The mixed bed ion exchange approach will work with almost any kind of cation exchanger and anion exchanger, regardless of their selectivity. Most ion exchangers are "nonspecific" meaning that they work principally due to electrostatic attraction between charges on the ion exchanger and those of solutes in the solution. Divalent cations such as calcium and magnesium have charge densities higher than monovalent cations and therefore are bound with greater affinity by most cation exchangers. In a water softener system for example, sodium-loaded polystyrene sulfonate (PS) will exchange sodium for calcium until the column is nearly completely exhausted. Similarly zirconium phosphate (ZP) used in the Redy® column for dialysate regeneration (produced by SORB Technology, a division of Fresenius Medical Care (FMC)) binds calcium and magnesium with higher affinity than potassium and ammonium. See Ash SR. Sorbents in treatment of uremia: a short history and a great future. Semin Dial. 2009 November-December; 22 (6):615-22. This doesn't mean that they don't bind any of the monovalent cations, but at physiologic concentrations a significant number of binding sites will be filled with divalent cations rather than monovalent cations.

To offset the removal of calcium and magnesium from the gut by cation exchanger and prevent low levels of these cations in the blood, it is possible to add calcium and magnesium salts to the mixture. A combination of calcium acetate and magnesium carbonate is already marketed by FMC as a phosphate sorbent (OsvaRen). The ingestion of magnesium and calcium salts also binds some phosphate, as a side benefit. If calcium and magnesium salts are administered with a mixed bed sorbent containing PS or ZP, the overall schema is that shown in FIG. 17.

For the mixed-bed system to work, it is preferable that the particles of cation and anion exchanger are kept in close proximity, throughout passage through the upper GI tract. This is to assure that the released $H^+$ and $OH^-$ will bind immediately to form water. Further the very low pH of the cation exchanger alone and the very high pH of the anion exchanger could be damaging to the gut (although purely hydrogen-loaded sodium polystyrene sulfonate has been given to patients for removal of potassium in the past in a clinical trial). Fortunately, cation and anion exchangers have opposite surface charges and tend to clump together naturally. Administering the two components as a mixture may keep particles in close enough proximity to maintain a neutral pH throughout the intestinal passage. Further, there are methods of granulation in common use in medicinal chemistry that should work well to maintain proximity of the mixed bed components.

FIG. 17 shows the basic concept of the combined sorbent system for a mixture containing non-specific ion exchangers, with the cation exchanger loaded with hydrogen and the anion exchanger loaded with hydroxide. For example, we have indicated that the cation exchanger could be either H-PS or H-ZP and the anion exchanger could be OH-ZO. SORB Technology has developed a form of ZO that allows complete loading of the anion exchanger with hydroxide without any damage to the ZO. Cations such as sodium, potassium, ammonium, calcium, and magnesium are bound by the cation exchanger, releasing hydrogen. Anions such as phosphate, sulfate, and chloride are bound by the anion exchanger, releasing hydroxide. The hydrogen and hydroxide combine to form water, which has no effect on concentration of cations or anions. The counter-ions of ion exchange, hydrogen and hydroxide, form water and disappear, creating a persistently high mole fraction concentration of each bound cation. FIG. 17 also shows the expectation that the removal of calcium and magnesium from patients with kidney failure would occur with these sorbents. This may not be needed and might be detrimental in some patients. To offset the removal of the divalent cations they can be provided separately as various salts, or as salts included within the sorbent mixture. The choice of calcium acetate and magnesium carbonate is a logical one, since these compounds are already included in a product that is given to patients with kidney failure to absorb phosphate (OsvaRen by FMC Medical). Enough of the calcium and magnesium remains soluble in the gut in patients taking this medication that the serum calcium and magnesium levels usually rise, limiting the amount that can be safely taken. In combination with H-PS or H-ZP and OH-ZO, phosphate would be bound by the calcium and salts, but serum calcium and magnesium levels would not rise. With this approach some of the binding sites are "wasted" by ion exchange for calcium and magnesium, but less than half of all sites.

FIG. 18 shows an alternative embodiment of our invention. In this approach the cation exchanger is partially pre-loaded with calcium and magnesium in the amounts that are expected to be bound within the gut. This will preclude removal of any calcium and magnesium from the patient. As in FIG. 17, the binding of the monovalent toxins per gram of sorbent mixture is diminished somewhat by the pre-loading of sites with calcium and magnesium, but the mixture will still be highly efficient because of the disappearance of the counter-ions hydrogen and hydroxide. Note that the calcium- and magnesium-loaded sites on the cation exchanger are not expected to exchange cations with the gut, and in order to provide an equal amount of exchangeable sites on both the cation and anion exchanger we have depicted use of a smaller amount of the anion exchanger than the cation exchanger (in terms of exchange capacity). Alternatively of course, the amount of cation exchange capacity could be increased versus that of the anion exchanger.

FIG. 19 shows the combination of hydrogen loaded ZS9 (H-ZS9) with a hydroxyl-loaded anion exchanger such as zirconium oxide (OH-ZO). Since ZS9 has essentially zero affinity for calcium and magnesium, these cations will not be removed from the gut, so they do not need to be replenished by oral administration. Since binding sites on ZS9 are not filled with calcium or magnesium, all the sites are available to bind sodium, potassium and ammonium. Binding of phosphate by ZO provides capability to remove phosphate from the gut and the patient. Due to the product of water from counter-ions hydrogen and hydroxide, the binding capacity of both the cation and anion exchangers is increased. This schema is shown in FIG. 19.

Because of the particular advantages of using a monovalent-selective cation exchanger in our mixed ion exchanger system, and because of our association with the ZS9 product, our initial in vitro tests of the system were performed with a combination of H-ZS9 and OH-ZO. Results are described below.

Summary of In Vitro Feasibility Trial of ZS9/ZO as a Mixed Ion Exchanger Sorbent ZS9 was provided in partially protonated form, and then equilibrated it in 0.05 M HCl for 14 hours, to further protonate the ZS9. Even with this further protonation step, the compound tested still contained some sodium.

A small quantity (1×) of equal parts of mostly protonated ZS9 and OH-loaded ZO was equilibrated with solutions simulating the concentrations of ions and uremic toxins in the gut during kidney failure:

| Solution | Small Bowel | Colon |
| --- | --- | --- |
| pH | 8.0 | 7.1 |
| KCl | 6.0 mM | 70.0 mM |
| NaCl | 98.0 mM | |
| NaHCO$_3$ | 40.0 mM | 30.0 mM |
| KH$_2$PO$_4$ | 2.5 mM | 20.0 mM |
| NH$_4$Cl | | 15.0 mM |
| Solution volume | 250 mL | 250 mL |
| ZS9 amount | 0.727 g | 0.436 g |
| ZO amount | 0.727 g | 0.436 g |

Calcium and magnesium were omitted from these test solutions because ZS9 is known not to bind these divalent cations, and to avoid creating a precipitate with the NaHCO$_3$. The results of the tests were expressed in terms of millimoles of cation or anion bound per gram of relevant sorbent (ZS9 for cations; ZO for anions). A summary graph of these experiments is shown in FIG. 20. The sorbent mixture removed a substantial amount of bicarbonate from the colon solution. This bicarbonate removal might be larger with completely protonated ZS9 but can be eliminated by providing a slight excess of OH-loaded ZO. Phosphate removal was highly effective, with about 2.0 mmole phosphate removed per gram of ZO. Current phosphate-removing oral sorbents such as sevelamer or calcium acetate remove less than 1 mM phosphate per gram. Potassium removal was about 4.2 mmole per gram ZS9. This is far greater than the amount of potassium bound by ZS9 in our clinical trials (less than 1 mEq/gram) which resulted in a decrease in urinary potassium of about 20 mEq/day in subjects ingesting 30 grams per day of ZS9. The ZS9/ZO combination also bound some ammonium, at about 0.35 mmole/gram of ZS9. We expect a higher amount of binding of ammonium when the sorbent mixture is in the gut, based on our human studies which demonstrated a significant decrease in serum urea levels at modest amounts of ingested ZS9. The in vitro studies also demonstrated that the ZS9/ZO mixture bound 0.65 mmole/g of sodium in the simulated small bowel fluid and released 0.17 mmole/g of sodium within the colon solution. In short, the mixed ion exchange system using ZS9-H and OH-ZO worked just as expected, and was remarkably powerful in binding uremic toxins.

In summary, our in vitro study indicates that the combination of a hydrogen-loaded cation exchanger (ZS9) and hydroxide-loaded anion exchanger (ZO) greatly increases the toxin-binding capacity of both sorbents, and should function well when administered orally as a combination in suspension. It appears that the ZS9/ZO combination could effectively remove enough uremic toxins to delay need for dialysis in many patients, obviate need for dialysis in other patients, and make the dialysis process much simpler for those patients who do progress to uremia and need hemodialysis or peritoneal dialysis. The use of combined cation exchangers and anion exchangers as oral sorbents is an entirely new concept in therapy. The oral therapy is even more unique and new when the cation exchanger is microporous zirconium silicate and the anion exchanger is zirconium oxide.

A distinct advantage of using ZS9 in the mixed bed sorbent is that ZS9 will not bind significant amounts of calcium or magnesium, which are usually not abnormally high in ESRD patients and would need to be replaced if they are depleted by the sorbents. Another advantage is that ZS9 is a crystal and therefore releases almost no zirconium into the solution. However, a disadvantage of ZS9 is that it will likely be expensive to produce, making the overall therapy somewhat costly. Therefore our studies turned to investigating the combination of ZP and ZO as an oral sorbent.

Zirconium Phosphate Multi-Ion Exchange Summary

ZP and ZO Combination for Therapeutic Electrolyte Balancing

1. Overview

One consequence of ESRD is an imbalance of electrolytes in blood and body fluids. Circulating body fluids exchange components with the contents of the gastrointestinal system and are thereby accessible to modification by orally administered dietary supplements. Zirconium-based ion exchange materials have capacity for the common electrolytes that are imbalanced in ESRD. The ultimate goal is restoration of healthy electrolyte balance in the patient by changing the gastrointestinal contents using a mixture of cationic and anionic ion exchangers.

Given the wide variation in concentration of all chemicals in the gut, it is desirable to be able to predict the binding of these toxins in varying chemical conditions. To do this, the first investigation was the performance of cation exchange materials in simple conditions. The cation exchanger, initially loaded with one cation, was equilibrated with a solution containing only one other cation. Secondly, a mixture of cation and anion exchange materials was added to solutions that approximate the electrolyte composition of GI contents. Specifically, mixtures of hydrogen-loaded cation exchanger and hydroxide-loaded zirconium oxide were incubated in solutions that simulate small bowel and colon conditions. Changes in the solutions after equilibration were measured. Thirdly, ion exchange performance of the sorbents in the simulated GI solutions was compared to what would have been predicted from the binary exchange experiments.

Materials used in this series of studies are the cation exchanger zirconium phosphate (ZP) and the anion exchanger zirconium oxide (ZO). This disclosure is primarily about cationic exchange material ZP because the cation imbalance is the most important and difficult to manage. ZP was investigated in greatest detail because it was used extensively in the Sorb column to regenerate dialysate. In this application, there were no clinical abnormalities ascribed to either ZP or zirconium in dialysate. Further, ZP was available in the high quantity at modest cost. Also, our experience with ZS9 showed that inorganic ion exchange materials were quite palatable when taken orally as a suspension in water. This disclosure also includes further analysis of the experiments that included ZS9, described above.

Cations of interest in these investigations are hydrogen, sodium, potassium, calcium, magnesium, and ammonium. The anions that were studied were hydroxide, chloride, and phosphate.

2. Executive Summary

Zirconium phosphate was evaluated in-vitro as a cationic intestinal sorbent for treating electrolyte imbalances.

The most important tests used a combination of ZP and the anion exchanger ZO. The combination is beneficial for two reasons. First, the anion exchanger can release hydroxide to neutralize hydrogen released by the cation exchanger, thus preventing acidification of the GI contents. Secondly, anions such as phosphate commonly need to be removed from the GI contents and patients, and ZO is a powerful sorbent for phosphate.

Solutions representative of small bowel and colon ionic concentrations were treated with a mixture of ZP and ZO. Results are shown in Table 5.

From small bowel solution, the cation removal (mEq/g ZP) was, in this order: sodium (4.62)>magnesium (0.92)>potassium (0.67)>calcium (0.57).

From colon solution, the cation removal was much greater, in this order: potassium (5.3)>magnesium (1.6)>calcium (1.0), ammonium (0.4). Sodium was released by the sorbents, 0.2 mEq/g ZP.

The amount of cation bound to ZP at small bowel concentrations is, from greatest to least, as shown in Table 9: sodium>hydrogen>calcium>magnesium>potassium. The amount of cation bound to ZP at colon concentrations is, from greatest to least: potassium>hydrogen>sodium>calcium>magnesium>ammonium.

The cation affinity series is, from greatest to least (Table 8), for small bowel: hydrogen>calcium>potassium>magnesium>sodium; for colon solution: hydrogen>calcium>sodium>potassium>magnesium.

The reason why the amount bound does not match the affinity series is that the difference in cation concentrations in physiologic solutions overwhelms the affinity differences.

A simple model based on individual ion exchange reactions was used to predict the performance in multi-ion solutions. This simple binary exchange model predicts that the cation amount bound by ZP would be greater in colon solution than in the small bowel solution. The experimental data showed the same trend at approximately the same magnitude of change. The ZP/ZO mixture exchanged much more sodium, potassium, calcium, magnesium, hydrogen and phosphate in the simulated small bowel and colon solutions than expected from the simple model of ZP binary exchange. Only ammonium exchange was close to the predicted amount. The reason for the increased binding of various cations was due principally to maintenance of neutral pH, caused by the neutralization of hydrogen by hydroxide released from ZO in association with the cation exchanger. With titration of ZP alone back to neutral pH in the physiologic solutions, its binding was increased to be similar to that of the mixture of ZP and ZO.

3. Binary Ion Exchange Testing

ZP was tested in simple situations to give a basis for predicting its performance in physiological conditions. Multi-component ion exchange is a complicated process and simulations and prediction of ion exchangers require fundamental performance data including single-component exchange. This series of studies consisted of binary exchange of individual cations with sodium- or hydrogen-loaded ZP.

Background

Representative in-vivo electrolyte concentrations are shown in Table 1. The colon concentrations for normal subjects were reported by Oliver Wrong and co-workers. See Wrong, O, & Metcalfe-Gibson, A, The electrolyte content of faeces. Proc R Soc Med. 1965 December; 58(12): 1007-1009. Note that in the data from the human studies, the anion and cation amounts are not equal. The authors attribute this to unmeasured anions and experimental error.

Conditions in the small bowel are estimated from average dietary intake and reported values. Calcium and magnesium values reflect a meal with high content of these electrolytes.

TABLE 1

| Human Physiological Conditions | | | | | |
|---|---|---|---|---|---|
| Cation | Small Bowel mEq/L | Colon mEq/L | Anion | Small Bowel mEq/L | Colon mEq/L |
| $NH_4$ | 14.0 | 14.0 | Bicarb | 30.0 | 32.0 |
| Ca | 8.0 | 27.0 | Cl | 152.0 | 16.0 |
| Na | 138.0 | 32.0 | $PO_4$ | 2.5 | 20.0 |
| Mg | 8.0 | 47.0 | Sulfate | | 3.0 |
| K | 8.5 | 75.0 | Organic | | 179.0 |
| H | 1.0E−05 | 7.9E−05 | Total | 184.5 | 250.0 |
| Total | 176.5 | 195.0 | | | |
| pH | 8.0 | 7.1 | | | |

Experiment Design

The first binary exchange studies were the exchange of sodium for either potassium, hydrogen or calcium. These were done with 1.0 gram sodium-loaded ZP in 10 mL of a solution of either KCl, HCl, or $CaCl_2$. Cation solutions in a 1,000-fold concentration range were used in order to test of the exchange behavior in almost all possible conditions.

A second series of experiments tested cation and anion exchange of ZP in simulated solutions representing normal small bowel and colon fluid solutions. These solutions included combinations of calcium, potassium, hydrogen, ammonium, sodium, magnesium and phosphate. These studies were done with cation concentrations in the range of physiological concentrations using 1.0 gram ZP in 100 mL or 200 ml of solution. The sorbent to volume ratio was changed for two reasons. First, the full concentration range is not necessary for this project. Understanding ion exchange performance at small bowel and colon conditions is adequate for therapeutic purposes. Secondly, the amount of cation in 10 mL solution was inadequate for the sorbent capacity. The ZP exchanged so much cation in the 10 mL solution that the equilibrium concentrations were very different than the physiological conditions, and therefore not representative of the expected patient response. Combinations that were tested under these conditions were sodium-loaded ZP with either hydrogen, ammonium, or magnesium. Hydrogen-loaded ZP was exchanged with sodium. Further refinements in the magnesium exchange experiments are described in detail below.

Materials

ZP and ZO were produced by the SORB Technology subsidiary of Fresenius Medical Care-NA.

The starting cation exchange material for these studies was ZP that was sodium loaded by SORB Technology. The potassium study was done with unmodified SORB material. Subsequent studies were done with ZP that was further sodium loaded by incubation in concentrated NaCl, then washed with deionized water (DIW). Sodium capacity of the ZP material was reported by SORB as 3.54 mEq/g.

Hydrogen-loaded ZP was used for investigation of sodium capacity. Acidified ZP material from SORB was further hydrogen loaded by incubation in 200 mM HCl for an hour, followed by thorough washing with DIW.

Hydroxide-loaded ZO was used as supplied by SORB Technology.

Analytical Methods

Sodium and potassium can be directly and simultaneously measured at HemoCleanse Technologies (HCT) using the BWB Technologies (United Kingdom, available at http://www.bwbtech.com/) flame photometer (FP). Calcium mutually interferes with the BWB FP measurement of both $Na^+$ and $K^+$, so it must be removed from the solutions before they are assayed. The BWB recommended method for calcium removal is precipitation using ammonium oxalate.

Two methods for calcium measurement were used. Calcium can be measured using the FP in the absence of $Na^+$ and $K^+$ after dissolving the calcium oxalate precipitate with perchloric acid. An alternate method is a spectrophotometric assay kit, TECO Diagnostics C503 (Anaheim, Calif., available at http://www.tecodiagnostics.com/clinical-use), which is simple and inexpensive, and measures $Ca^{++}$ in the presence of $Na^+$ and $K^+$. Both methods require dilution of the sample so that it is in the linear concentration range of the test. TECO kit assay is preferable because it requires fewer steps of sample preparation.

Magnesium, ammonium, phosphate, and chloride were measured using the TECO Diagnostics kits M527, B551, I515, and C501, respectively. These are simple procedures: all except ammonium are a one-step reaction and ammonium assay is a two-step reaction.

Hydrogen is measured with a pH meter. Suspensions containing sorbents can take up to 30 minutes for the pH reading to stabilize.

Some samples were also sent to Spectra Laboratories (Milipitas, Calif.) to be assayed under GLP conditions. Spectra can analyze for $Na^+$, $K^+$, $Ca^{++}$, $Mg^{++}$, $Cl^-$, pH, and phosphate, but ammonium assay is not available. Because Spectra assays clinical samples and their instruments are setup to measure in physiological ranges, they cannot accurately measure samples that are below the physiological range. Therefore, Spectra is mostly useful for corroborating assays done in-house. In many cases, assays done at Hemo-Cleanse looked as reliable as the results from Spectra, based on assays of the small bowel and colon solutions.

Binary Exchange Data Analysis and Observations

A standard analysis of ion exchange data is the plot of the amount of solute bound to the sorbent as a function of the equilibrium concentration of the solute in solution, at constant temperature. Hence, these relationships are often referred to as isotherms. For comparative purposes, solution concentrations are normalized by expressing them as the normality of the ion of interest divided by the total normality of the solution; this ratio is called the equivalent fraction. By design, isotherm plots all start at the origin (nothing exchanged when nothing to exchange is present) and end where the ion exchange material is completely occupied with the ion which is the only one in solution (i.e., the solution fraction of the exchanging ion is 1.0 and the amount bound is the maximum capacity of the ion exchanger).

Isotherms for binary exchange of Na-loaded ZP with $K^+$, $Ca^{++}$, $H^+$, $NH_4^+$ and $Mg^{++}$ and hydrogen-loaded ZP with $Na^+$ are shown in FIGS. 1-6 and are discussed individually below. Exchanges of one cation with another on ZP were done in several conditions that produced equilibrium concentrations bracketing the physiological equivalent fractions of the small bowel and colon. In order to make realistic comparisons of the performances of the various cations, linear correlations of the experimental data in the physiological range were computed. The expected binding at small bowel and colon conditions was calculated from these linear correlations.

Linear modeling simplifies the data and calculations based thereupon. The isotherm plots usually show some data outside the physiological range in order that the plots can have the same dimensions, facilitating easy visual comparison. As seen in some of the isotherms, the behavior of ion exchangers at low and high equivalent fractions can be quite non-linear. It is unlikely that the sorbents will be exposed to those conditions so most of those data are not included in calculations and analysis.

After the experiments were completed, we realized that the standard format for presenting, analyzing, and using binary exchange data requires a constant normality of the solution, also called total ionic strength (TIS). See Helfferich, Friedrich. *Ion Exchange*. Mineola, N.Y.: Dover Publications, 1995. Originally published in English: New York: McGraw-Hill, 1962. Ion exchange capacity is inversely related to the TIS and this effect is most noticeable at very low TIS. The ionic strength is also indicated on the binary exchange graphs.

The experimental ion exchange data can be qualitatively compensated for its total ionic strength outside the physiological range as follows. The experimental ion exchange data at low equivalent fraction, (where experimental TIS is low), is greater than the ion exchange expected at physiological TIS. Conversely, where experimental TIS is higher than physiological, the amount bound would be slightly higher in a more realistic simulated in-vivo conditions.

Binary Exchange Summary

The expected cation binding to ZP at small bowel and colon conditions are presented in Table 2. Sodium is bound in the greatest amount in both conditions. Hydrogen is second and third in amount bound in small bowel and colon solutions, respectively. Potassium and calcium are present in much higher concentration in colon than small bowel, thus producing higher amounts bound.

"Total Cations Bound" is simply the sum of the amounts bound in the individual binary exchanges; it is not an experimental result. Note that the sum of the total cation binding predicted for the two conditions is similar, though the computed total binding is higher in colon conditions than small bowel.

TABLE 2

Cations bound to ZP during binary exchanges
Computed amount bound at physiological
concentrations, mEq/gram ZP

| Small Bowel | | Colon | |
| --- | --- | --- | --- |
| Sodium | 3.72 | Sodium | 2.47 |
| Hydrogen | 1.56 | Potassium | 1.92 |
| Calcium | 0.38 | Hydrogen | 1.56 |
| Potassium | 0.26 | Calcium | 1.08 |
| Magnesium | 0.04 | Ammonium | 0.39 |
| Ammonium | N/A | Magnesium | 0.20 |
| Total Cations Bound | 5.96 | Total Cations Bound | 7.62 |

Potassium/Sodium Exchange: ZP-Na+KCl=ZP-K+NaCl (FIG. 1)

Exchange of $Na^+$ for $K^+$ was nearly equimolar, as expected.

The linear model of potassium binding fits the data well. Compensating for the total ionic strength would improve the linear fit to the data, especially at the low equivalent fraction in solution, where the binding is higher than would be expected at physiological total ionic strength.

Calcium/Sodium Exchange: 2 ZP-Na+CaCl$_2$=ZP-Ca+2 NaCl (FIG. 2)

Calcium is expected to have a very high affinity for ZP. The modest binding under physiological conditions is primarily due to its low concentration.

Our assays showed that Ca$^{++}$ and Na$^+$ did not exchange in equal equivalents; calcium binding was approximately 15 times greater than sodium release. Data in the chart are averages of consistent, replicated data.

Magnesium/Sodium Exchange: 2 ZP-Na+MgCl$_2$=ZP-Mg+2 NaCl (FIG. 3)

This study was done in 154 mM NaCl with added Mg$^{++}$ in various initial concentrations bracketing the in-vivo Mg$^{++}$ concentrations. This was done to more closely and consistently approximate total ionic strength of physiological conditions of Mg$^{++}$ binding than was done with the other cation exchange experiments. Sodium in solution will compete with Mg$^{++}$ for binding on ZP, but that will happen to a similar extent in-vivo.

Magnesium exchange was very low in these experiments. Mg$^{++}$ and Na$^+$ exchanged in approximately equal equivalents per gram.

Ammonium/Sodium Exchange: ZP-Na+NH$_4$Cl=ZP-NH$_4$+NaCl (FIG. 4)

Ammonium exchange with Na-loaded ZP was very close to equimolar exchange. Ammonium capacity was also low.

Ammonium concentration in small bowel was considered to be negligible for this set of experiments and therefore was not included in the solution. That is why only colon conditions are plotted in FIG. 4.

The very low total ionic strength of this experiment may compromise the predictive value of this data. Binding at the ammonium equivalent fraction with physiological total ionic strength is expected to be lower than the reported data.

Sodium Binding to ZP: ZP-H+NaOH=ZP-Na+H$_2$O (FIG. 5)

Hydrogen-loaded ZP was titrated with 0.2 M NaOH. Assays of the solution showed equimolar exchange between the ZP-H and sodium in solution. The solution pH and Na$^+$ content were measured. Sodium content of the sorbent was computed from the disappearance of both Na$^+$ and OH$^-$ from the solution; both measurements were in very close agreement. Hydroxide disappearance was considered to be the result of it being neutralized by hydrogen released from the ZP in exchange for sodium. Hydroxide concentration is calculated from pOH=14−pH=−log$_{10}$([OH$^-$]). Rearranged and solving for hydroxide concentration, [OH—]=10$^{pH-}$14.

Sodium content of the ZP was computed from the maximum sodium that could be loaded on the ZP plus the change in concentration of Na$^+$ in the incubation solution. Note that the sodium bound to ZP is well-represented by a linear model in the physiological concentration range. However, the linear model does not hold at the low and high sodium mole fractions. At high NaOH concentrations, the neutralization of the hydroxide by hydrogen may be the driving force for hydrogen release from the ZP that opens up sodium binding sites.

Hydrogen Binding to ZP (FIG. 6)

ZP-Na+HCl=ZP-H+NaCl and ZP-H+NaOH=ZP-Na+H$_2$O

Hydrogen content of ZP was investigated with two experiments. (1) ZP-Na was treated with HCl to displace the Na$^+$ with H$^+$. (2) ZP-H was treated with NaOH to displace the H$^+$ with Na. In this experiment, which is not the reverse of experiment 1, the production of water by the combination of the displaced H$^+$ with the OH$^-$ in the solution drives the equilibrium towards binding Na. Data in the pH range of 6.1 to 7.9 was selected to generate a linear relationship between hydrogen bound and hydrogen equivalent fraction, shown as "ZP-H+NaOH select" on the chart. Selected data are shown as brown crosses and brown dashed line. The linear relationship is not a straight line on the chart because the x-axis is logarithmic.

Note that the linear projection from the ZP-H+NaOH experiment comes very close to the data in the physiological range from the other experiment.

Phosphate Binding of ZO OH-ZO+KH$_2$PO$_4$=ZO-KHPO$_4$+H$_2$O (FIG. 15)

Binding of phosphate is quite linear over the range of solution fractions displayed in the figure, but it was not tested at the low end, at the in-vivo range. The linear estimate of phosphate binding in the physiological range is likely to overestimate the binding.

4. Multiple Ion Exchange Using ZP in Simulated Physiological Conditions

Overview

It is possible to predict the ion exchange in-vivo from the simplest and most general characteristics of the sorbents. The simplest experiments, described above, are the binary exchange experiments at equilibrium. Progressing towards a more realistic situation, the equilibrium ion-exchange performance of the sorbents in simulated physiological conditions was tested to see how well it could be predicted from the binary exchange results.

Experiment Design and Procedure

Sorbent performance in the multiple-ion conditions was measured using hydrogen-loaded ZP alone or in combination with hydroxide-loaded ZO. The combination of H-ZP and OH-ZO is envisioned as the therapeutic regimen. When H-ZP and OH-ZO are used in combination, the hydrogen and hydroxide displaced by the respective cations and anions will combine to form water, will tend to maintain a physiological pH, and will favor the exchange going to completion.

Sorbents were equilibrated in the small bowel or colon solution at 37° C. with vigorous shaking (300 RPM) for at least 3 hours. Sorbent quantity was always 1.0 gram for each sorbent, either H-ZP alone or H-ZP plus OH-ZO. The volume of solution was either 100 or 200 mL.

After the sorbents were equilibrated with the solution, a large sample of solution was filtered through a 0.2 micron filter to remove the sorbent. The filtered supernatant was refrigerated until it was assayed.

Materials: ZS9 Experiments

This disclosure also includes some further analysis of the above-described experiments on the performance of zirconium silicate (ZS9) Sorbents used included ZS9 and ZO.

ZS9 was commonly protonated by treating 50 g ZS9 with 1,000 mL 0.05M HCl with vigorous shaking for several hours. Hydrous OH-ZO from SORB was used without modification.

The ZS9 experiments were done in 250 mL with equal amounts of H-ZS9 and OH-ZO; small bowel solution had 0.727 grams of each sorbent; colon solution had 0.436 grams of each sorbent. The ratio of solution to sorbent was 344 for small bowel and 573 for colon.

It should be noted that ZS9 is specifically formulated and synthesized to exclude calcium and probably also has negligible capacity for magnesium. That is why Ca++ and Mg++ were not included in the test solutions for the ZS9/ZO.

Materials: ZP Experiments

Starting material was the same as used for the binary exchange experiments, above.

Sorbents used included ZP and ZO. Partially acid-loaded ZP (100 grams) from SORB was incubated in 400 mL 0.200 M HCl for 1 hour at 37° C. with vigorous shaking (300 rpm), filtered with minimal washing, and dried. This treatment significantly increased the acid loading of the ZP. Hydrous OH-ZO from SORB was used without modification. Subsequent work has shown that this material has additional capacity for hydroxide. Sorbents were used in 1.0 gram quantities were incubated in 100 mL or 200 mL of test solution for 3 hours at 37° C. with vigorous shaking (300 rpm).

The ratio of solution to sorbent was 100 for small bowel and either 100 or 200 for colon.

Materials: Test Solutions

Typical physiological colon conditions include bicarbonate (32 mEq/L), calcium (27 mEq/L), and magnesium (47 mEq/L). This composition cannot be duplicated in-vitro because the bicarbonate is precipitated by the cations, producing a cloudy suspension. Therefore, in the test solutions, the bicarbonate was replaced by sodium chloride. Sulfate concentration is low and is therefore not duplicated. Organic anions are large, diverse, and undefined category that are, along with sulfate, replaced in this study by chloride. Unlike the data in Table 1, the total cation concentration in our solutions must necessarily equal the total anion concentration.

TABLE 3

Simulated Digestive Conditions: Starting solutions for ion exchange

| | Sorbent | | | | |
|---|---|---|---|---|---|
| | ZP Small Bowel | ZP Colon | ZS9 Small Bowel | ZS9 Colon | |
| KCl | 6.0 | 70.0 | 6.0 | 70.0 | mM |
| KH2PO4 | 2.5 | 20.0 | 2.5 | 20 | mM |
| NH4Cl | | 15.0 | | 15 | mM |
| NaCl | 138.0 | 30.0 | 98 | | mM |
| CaCl2 | 4.0 | 13.5 | | | mM |
| MgCl2 | 4.0 | 23.5 | | | mM |
| NaHCO3 | | | 40.0 | 30.0 | mM |
| Na+ | 138.0 | 30.0 | 138.0 | 30.0 | mEq/L |
| K+ | 8.5 | 90.0 | 8.5 | 90.0 | mEq/L |
| NH4+ | | 15.0 | | 15.0 | mEq/L |
| Ca++ | 8.0 | 27.0 | | | mEq/L |
| Mg++ | 8.0 | 47.0 | | | mEq/L |
| Cl− | 160.0 | 189.0 | 104.0 | 85.0 | mEq/L |

TABLE 3-continued

Simulated Digestive Conditions: Starting solutions for ion exchange

| | Sorbent | | | | |
|---|---|---|---|---|---|
| | ZP Small Bowel | ZP Colon | ZS9 Small Bowel | ZS9 Colon | |
| PO4−− | 2.5 | 20.0 | 2.5 | 20.0 | mEq/L |
| HCO3− | | | 40.0 | 30.0 | mEq/L |
| Total | 162.5 | 209.0 | 146.5 | 135.0 | mEq/L |

Starting pH of the test solutions for small bowel was 4.65 and for colon was 4.36. The pH of the colon solution could not be adjusted to closer to physiological pH by the addition of NaOH without generating a precipitate. During equilibration, the solutions became more acidic (pH decreased). Before the solutions were sampled for electrolyte assay, the pH was adjusted by addition of NaOH to produce the desired physiological pH: small bowel=8.00 and colon=7.10. This reduced the difference between experimental and in-vivo conditions, but precipitates were not formed because much of the calcium was already bound to the sorbents. The colon formulation above differs from physiological concentrations in the literature primarily in its higher $[K^+]$ (90 vs. 75 mM) and minor differences in $[Na^+]$ (30 vs. 32 mM) and $[NH_4^+]$ (15 vs. 14 mM). This formulation was used in prior experiments with zirconium silicate (ZS9) and its continued use was for the purpose of comparative performance of the two cation exchange materials. Results of the ZS9 studies are included in FIG. 7 and FIG. 8, and some of this data is repeated in FIG. 20.

For purposes of comparing the sorbent properties, the 200 mL volume of colon solution with the ZP/ZO combination is more representative because of the patient conditions have a very large reservoir of cations and unlike the 100 mL experiments are not likely to be mostly depleted of cation by orally administered sorbents.

Analytical Methods

Sodium and potassium were measured using the BWB flame photometer; pH was measured with pH meter.

All the other cations and anions were measured using TECO Diagnostics spectrophotometric assays as described above.

Data Analysis and Observations

Sorbent performance was calculated from assayed concentrations, even when those assay results were different than expected values. This was especially the case for the calcium and phosphate data below. Solutions did not start at physiological pH and after equilibration were at "Post pH". To more accurately represent physiological conditions, NaOH was added to adjust the pH of the equilibrated solution to patient pH. The sodium content of the added NaOH was subtracted from the measured Na to produce a more accurate estimate of Na binding by sorbent.

TABLE 4

Equilibrated Supernatant Concentrations, mEq/L @ Final pH

| Solution | Volume, mL | Sorbent | Na | K | Ca | Mg | NH4 | H+ | PO4 | Cl | Post pH | mEq NaOH added | Final pH |
|---|---|---|---|---|---|---|---|---|---|---|---|---|---|
| DIW | 100 | ZP | 1.0 | 0.0 | 0.1 | 0.1 | 0 | 1.51 | 0.9 | 0.7 | 2.8 | | |
| DIW | 100 | ZP & ZO | 0.8 | −0.1 | 0.3 | 0.1 | 0 | 0.00 | 0.0 | 1.1 | 5.4 | | |
| Small Bowel | 100 | ZP | 136.7 | 3.0 | 1.9 | 4.0 | 0 | 8.00 | 1.7 | 134.0 | 2.1 | 4.7 | 8.0 |

TABLE 4-continued

Equilibrated Supernatant Concentrations, mEq/L @ Final pH

| Solution | Volume, mL | Sorbent | Na | K | Ca | Mg | NH4 | H+ | PO4 | Cl | Post pH | mEq NaOH added | Final pH |
|---|---|---|---|---|---|---|---|---|---|---|---|---|---|
| Small Bowel | 100 | ZP & ZO | 135.7 | 3.2 | 0.2 | 1.0 | 0 | 0.61 | 0.0 | 136.8 | 3.2 | 4.4 | 8.1 |
| Colon | 100 | ZP | 78.1 | 50.3 | 2.0 | 21.2 | 8.80 | 6.31 | 5.3 | 135.6 | 2.2 | 7.1 | 7.1 |
| Colon | 100 | ZP & ZO | 63.8 | 55.6 | 4.1 | 30.1 | 12.33 | 0.26 | 0.1 | 138.5 | 3.6 | 3.4 | 7.1 |
| Colon | 200 | ZP & ZO | 55.5 | 73.4 | 5.0 | 30.7 | 13.54 | 0.24 | 2.5 | 144.4 | 3.6 | 4.7 | 7.1 |

For ease of comparison, the data of Table 4 is processed to show in Table 5 how much electrolyte was exchanged per weight of sorbent. As expected, deionized water has a very small effect on the sorbents.

TABLE 5

Amount changed in Solution: mEq/gram ZP. (−) = binding to sorbent; (+) = release. Na contributed by NaOH is subtracted from Na results.

| Solution | Solution Ratio | Sorbent | Na | K | Ca | Mg | NH4 | Equil H+ | PO4 | Cl | Total Cation | Total Anion |
|---|---|---|---|---|---|---|---|---|---|---|---|---|
| DIW | 100 | ZP | 0.10 | 0.00 | 0.01 | 0.01 | 0.00 | 0.02 | 0.09 | 0.07 | 0.13 | 0.16 |
| DIW | 100 | ZP & ZO | 0.08 | −0.01 | 0.03 | 0.01 | 0.00 | 0.00 | 0.00 | 0.11 | 0.11 | 0.11 |
| Small Bowel | 100 | ZP | −4.85 | −0.69 | −0.40 | −0.58 | | 0.08 | −0.08 | −0.68 | −6.43 | −0.76 |
| Small Bowel | 100 | ZP & ZO | −4.62 | −0.67 | −0.57 | −0.92 | | 0.01 | −0.25 | −0.40 | −6.76 | −0.65 |
| Colon | 100 | ZP | −2.36 | −4.95 | −1.26 | −2.25 | −0.84 | 0.06 | −1.47 | −1.87 | −11.59 | −3.35 |
| Colon | 100 | ZP & ZO | −0.12 | −4.42 | −1.05 | −1.70 | −0.46 | 0.00 | −1.99 | −1.59 | −7.76 | −3.58 |
| Colon | 200 | ZP & ZO | 0.19 | −5.28 | −0.97 | −1.64 | −0.37 | 0.00 | −3.50 | −1.00 | −8.06 | −4.49 |
| Small Bowel | 344 | ZS9 & ZO | −0.65 | −1.10 | | | 0.00 | 0.00 | −0.49 | | −1.75 | |
| Colon | 573 | ZS9 & ZO | 0.17 | −4.19 | | | −0.35 | 0.00 | −1.97 | | −4.37 | |

FIGS. 7 and 8 display the data from Table 5 which includes data from experiments with a mixture of ZS9 and ZO. The ZP/ZO performance in 200 mL colon solution is the most comparable to ZS9 performance because the amount of available cations for exchange is most similar.

In small bowel solution (FIG. 7), all of the sorbent-produced electrolyte changes are modest.

Detailed comments on each ion are included after Table 7, below.

FIG. 8 shows ion-exchange of 3 sorbent/solution combinations in the colon solution. It compares the performances of ZP alone and in combination with ZO, and ZS9/ZO. Largely due to the different initial concentrations, the sorbents have a much bigger impact on the colon solution than the small bowel solution.

Table 6 shows data from Table 5 processed to show the fractional change each electrolyte in the small bowel and colon solutions. High fractional change in solution concentration (highlighted) indicates that for some instances for calcium, magnesium, and phosphate, the ion exchange was nearly complete and the solution was mostly depleted of the cation. Therefore, the in-vivo sorbent performance could be significantly different than these results.

TABLE 6

Fractional Change of solution concentration

| Solution | Volume, mL | Sorbent | Na | K | Ca | Mg | NH4 | PO4 | Cl |
|---|---|---|---|---|---|---|---|---|---|
| Small Bowel | 100 | ZP | −0.01 | −0.69 | −0.68 | −0.59 | 0.00 | −0.15 | −0.05 |
| Small Bowel | 100 | ZP & ZO | −0.02 | −0.67 | −0.97 | −0.90 | 0.00 | −0.98 | −0.03 |
| Colon | 100 | ZP | 1.53 | −0.50 | −0.86 | −0.55 | 0.49 | −0.62 | −0.12 |
| Colon | 100 | ZP & ZO | 1.07 | −0.44 | −0.72 | −0.36 | 0.28 | −0.99 | −0.10 |
| Colon | 200 | ZP & ZO | 0.80 | −0.26 | −0.66 | −0.35 | 0.21 | −0.82 | −0.06 |

Table 7 shows data from Table 5 as processed to highlight the effect of combining ZO with ZP. The amount bound by the ZP alone was subtracted from the amount bound by the ZP/ZO combination, for each ion.

TABLE 7

Effect on physiological solution of ZP & ZO combination vs. ZP alone
Difference in amount bound, mEq/g: (+) = more bound by ZP & ZO

| Solution | ZP & ZO Volume | Na | K | Ca | Mg | NH4 | H+ | PO4 | Cl | Total Cation | Total Anion |
|---|---|---|---|---|---|---|---|---|---|---|---|
| Small Bowel | 100 | −0.23 | −0.02 | 0.17 | 0.34 | 0.00 | 0.07 | 0.17 | −0.28 | 0.34 | −0.11 |
| Colon | 100 | −2.24 | −0.53 | −0.21 | −0.54 | −0.38 | 0.06 | 0.51 | −0.28 | −3.84 | 0.23 |
| Colon | 200 | −2.55 | 0.33 | −0.30 | −0.61 | −0.47 | 0.06 | 2.02 | −0.88 | −3.53 | 1.14 |

The combination of cationic and anionic exchange materials did appear to affect the cation exchange. There are differences where the absolute value is greater than 1.0 mEq/g. That is a somewhat arbitrary threshold for substantial change, but this shows the biggest differences in this data. Overall the ZP alone had greater binding of cations. However the studies of ZP binding were performed after neutralization of the acidic solutions with sodium hydroxide. Use of sodium hydroxide to balance pH in the intestine of patients would not be safe, and would result in sodium loading. In the combination of ZP with ZO, hydroxide from ZO is what neutralizes the acidity produced by hydrogen released from ZP.

In the small bowel solution, the biggest individual ion difference was hydrogen. The hydrogen that decreases in the solution is not necessarily bound to ZP. More likely, it is neutralized by hydroxide from the ZO. Formation of water would favor the neutralization reaction. The effect of adding ZO to the sorbent on all the other ions is small but the total cation binding increased significantly, largely due to the hydrogen change.

The biggest effects on the colon solution of adding ZO to ZP were on the exchange of sodium, hydrogen, and phosphate. Lesser but probably significant effects were observed in all the other cations except calcium. The change in the cation total was modest, suggesting that equal equivalents of cations were exchanged.

Comments on Individual Ion Exchange Measurements (Tables 4, 5, 6, & 7 and FIGS. 7 & 8)

Sodium

Small Bowel. A large amount of sodium was removed from the small bowel solution by ZP and a much smaller amount by ZS9. The presence of ZO made a minimal decrease in Na binding.

Colon. ZP alone bound about half the ZP bound in the small bowel solution. ZO apparently released a large amount of sodium into all colon solutions: the net sodium change of the ZP/ZO was very small Na binding. ZS9/ZO released a very small amount of sodium.

Clinical implications. Large sodium binding in the small bowel followed by small change in colon by a ZP/ZO mixture is highly desirable. Sodium binding by the sorbents could easily be reduced, if necessary, by partial Na loading of ZP.

Potassium

Potassium behavior in the solution is only slightly affected by the presence of ZO in the sorbent mixture.

Small Bowel. ZS9 removed more potassium from the small bowel solution than ZP.

Colon. Due to the high potassium content of the colon solution, lots of potassium was exchanged for cations on the sorbents. ZS9 exchanged slightly less potassium than ZP.

Calcium

The solutions were depleted of $Ca^{++}$, sometimes severely, in all of the tests. The calcium capacity of ZP was very high compared to the amount of available $Ca^{++}$ in solution. This influences all of the $Ca^{++}$ results and the interpretation of them. ZO had only a small effect on calcium binding. A larger solution volume would have yielded more realistic results.

Small Bowel. Low calcium exchange with slight increase in presence of ZO.

Colon Slightly higher exchange than small bowel with slight decrease in presence of ZO.

Magnesium

Magnesium binding was greater than calcium in both solutions. This could be expected because [Mg++] was almost twice [Ca++]. Therefore, it would be harder to deplete all the Mg in solution. Mg++ is also more highly electronegative than Ca++ and has a smaller ionic radius and thus can access exchange sites that calcium cannot.

Small Bowel. Low amount of exchange was enhanced by ZO.

Colon. Modest amount of exchange was diminished by ZO.

Ammonium

Colon. Ammonium binding was very modest in these simulated intestinal solution experiments. Further, the binding decreased with the addition of ZO sorbent. As mentioned above clinical trials with ZS9 ingestion showed significant ammonium binding in the intestine, as reflected in a decrease in blood urea nitrogen levels in the patients. Therefore ammonium binding may be more active within the gut than in our simulated solutions. Modified cation exchangers are being developed which should greatly increase ammonium removal.

Hydrogen

Hydrogen in solution increased when only ZP was present, due to the easily exchanged $H^+$ on the ZP. When ZO was added to the mixture, the pH of the solution did not change very much because the $H^+$ was neutralized by the release of $OH^-$ from the ZO.

Hydrogen release by ZP was very similar in both small bowel and colon solutions. ZS9 released a very small amount of hydrogen in both solutions.

Phosphate

Small Bowel. Phosphate exchange by both ZP and ZP/ZO was very low, due to the low concentration of phosphate in the solution. ZS9/ZO removed a small amount of phosphate.

Colon. Phosphate binding by ZS9/ZO is less than or equal to binding by ZP/ZO. Phosphate binding increased with greater solution volume, largely due to depletion of phosphate at the lower volume. In the absence of an anion exchange material, phosphate change is expected to be minimal, as was the case in the small bowel solution. The surprising result was that with only ZP in the colon solution, 1.47 mEq/g PO4 is bound. This is probably due to the high [PO4] in the colon solution: it was 20.0 mM instead 2.0 mM, which is a realistic physiological concentration. The mistakenly high [PO4] would be expected to produce an elevated amount of ion exchange, which is probably not therapeutically significant; see further discussion of this data accompanying FIG. 16.

Chloride

Similar to hydrogen, the chloride concentration changes about half as much when both ZP and ZO are present, compared to ZP alone.

Total Cation and Total Anion

As shown in Table 5, sorbents always caused a decrease in the total cation and anion concentrations of both solutions. In small bowel solution, total cation loss was approx. 10 times anion loss. Total ion loss was greater for colon solution than small bowel solution; anion loss was much larger than in small bowel solution.

The net effect of the addition of ZO to sorbent is shown in Table 7. In the small bowel solution, the effect was to increase total cation removal by 0.34 mEq/g and a negligible effect on total anions. Net effect on both total cations and total anions was similar for both the 100 mL and 200 mL colon solutions. Total cation removal from colon solution decreased 3.84 and 3.53 mEq/g, respectively; total anion removal increased by 0.23 or 1.14 mEq/g.

Net removal of measured electrolytes indicates that the hydrogen- and hydroxide-loaded sorbents are working as expected. The initial loaded sorbents exchange their hydrogen and hydroxide for the other electrolytes and combine to form water, which we are not capable of measuring independently.

Binding Affinity

Table 8 summarizes the cation binding performance of the ZP/ZO mixture in the two physiological conditions of interest.

cantly higher than the binding in binary exchange experiments. This difference is largely due to the pH conditions of the binding. The binary binding studies must necessarily be done in an uncontrolled pH environment; buffering or adjusting pH would introduce additional ions. The multi-ion experiments were assayed after the pH was adjusted to physiologic level with NaOH.

In the multi-ion experiments, ZP alone bound slightly more cation than the ZP/ZO combined sorbent, except for sodium. The linear regressions through the respective data sets diverge widely, but the actual data, as seen on the individual charts and Tables 7 & 8 are close together. The divergence is mostly due to the linear extrapolation of data to much higher equivalent fraction than was achieved experimentally.

Note that the total cations bound as computed from experimental data is much higher than the expected capacity of the ZP, which was assumed to be approximately 4.0 mEq/g. However, that capacity is based on unknown test conditions and analysis that may not be comparable to those of this disclosure (such as a low pH level). Note that the total cations bound was higher in the colon solution than the small bowel. It was expected that the total binding capacity is unaffected by the surrounding solution. However, it seems that the total binding capacity is increased by the total concentration and interaction of solutes, as well as adjustment of the pH upwards to near neutral (discussed further below). The total concentration of the small bowel solution was 162.5 mEq/L and colon was 209 mEq/L. The interaction of the solutes may influence the measured total capacity of the ZP and ZO mixture.

Potassium (FIG. 9)

Potassium binding by ZP alone was slightly higher than the combination of ZP/ZO. These linear estimates are closer together than every other cation except sodium.

Calcium (FIG. 10)

ZP has a high affinity for calcium and therefore most of the calcium was depleted from the test solutions. One consequence of this is that the final calcium concentrations

TABLE 8

Cation Binding & Affinity

| | Small Bowel | | | | Colon | | | |
|---|---|---|---|---|---|---|---|---|
| Ion | mEq/L Final [Cation] | Equiv fraction | mEq/g Amount bound | Small Bowel Affinity | mEq/L Final [Cation] | Equiv fraction | mEq/g Amount bound | Colon Affinity |
| Calcium | 0.2 | 0.001 | 0.57 | 448.0 | 5.0 | 0.028 | 0.97 | 34.5 |
| Magnesium | 1.0 | 0.007 | 0.92 | 130.5 | 30.7 | 0.172 | 1.64 | 9.5 |
| Potassium | 3.2 | 0.023 | 0.67 | 28.8 | 73.4 | 0.412 | 5.28 | 12.8 |
| Sodium | 135.7 | 0.969 | 4.62 | 4.8 | 55.5 | 0.312 | −0.19 | −0.6 |
| Ammonium | | | | | 13.5 | 0.076 | 0.37 | 4.8 |
| Total | 140.1 | | 6.77 | | 178.1 | | 8.06 | |

Ion exchange affinity in this disclosure is defined as the amount of cation bound to ZP divided by its equilibrium solution fraction Calcium has the highest affinity. The amount of sodium released by the ZP in the colon solution is less than that removed by ZP in the small intestine solution.

5. Multiple Ion Exchange

General Observations (FIGS. 9-14)

The amount bound by sorbents from the multiple-ion simulated physiological solutions was in all cases signifiare much less than the physiological concentrations. The binary binding data fit a linear model pretty well throughout the physiological concentration range, so a linear projection may be reasonable.

Magnesium (FIG. 11)

When the multi-ion solutions equilibrated with the sorbents, the final magnesium concentrations were near the in-vivo mole fractions. Therefore, the binding expected on the basis of the empirical data should be reasonably reliable at small bowel conditions. The lowest value in the ZP/ZO data series may be somewhat artefactual due to the severely depleted $Mg^{++}$ in the test of small-bowel solution. If that is the case, the linear model of the ZP/ZO could be very different when tested with adequate solution so that the sorbent did not exchange most of the $Mg^{++}$.

Ammonium (FIG. 12)

Actual ammonium binding was closer to the binary binding prediction than the other cations.

The low amount of ammonium binding is a strong function of the low ammonium concentration. Clinical experience with intestinal sorbents indicates that ammonium binding in-vivo is much greater than what would be predicted from laboratory studies. Compare to Ash S R, Singh B, Lavin P T, Stavros F, Rasmussen H S. A phase 2 study on the treatment of hyperkalemia in patients with CKD suggests that the selective potassium trap, ZS-9, is safe and efficient. Kidney Int. 2015 August 88(2):404-11.

Sodium (FIG. 13)

Unlike the binary binding models for $K^+$, $Mg^{++}$, and $Ca^{++}$, the sodium binary binding model has a large non-zero intercept. Maybe the ZP has some residual sodium content, in whatever form it is prepared.

The sorbent mixture ZP/ZO has similar sodium binding to ZP alone in the physiological range.

Hydrogen (FIG. 14)

Hydrogen computed to be bound on ZP is nearly constant at in-vivo conditions and is not much different between ZP alone and the ZO& ZP combination. (The linear models are not straight on the graph because of the logarithmic scale.) When both anion and cation exchangers (ZP/ZO) are present, the pH change in the solution is small.

Phosphate (FIG. 16)

Data for phosphate binding to ZO brackets the physiological conditions. Empirical predictions of phosphate behavior can therefore be interpolated from the two actual data points nearest the in-vivo conditions: the ZP/ZO (2) data and its linear fit. The linear estimate from FIG. 15 is included with the data from the simulated patient solution results.

As with the cations, the binary exchange data underestimates the binding in multi-ion solution.

Proposed Predictive Method

The affinity values shown in Table 7 can be used to estimate the cation removal when the GI conditions are similar to the composition of the small bowel and colon solutions. The definition of affinity is:

$$\text{Affinity} = \text{Amount Bound per gram of sorbent/Solution Fraction}. \quad (1)$$

For GI conditions similar to test conditions, Affinity can be considered constant and the amount bound can be calculated from the re-arranged equation:

$$\text{Amount Bound per gram of sorbent} = \text{Affinity} * \text{Solution Fraction}. \quad (2)$$

Calculating the amount bound would be useful in determining appropriate patient inputs to promote therapeutic electrolyte balance. For example, it would be helpful to know what amount of sorbent would be needed to decrease the serum level of a toxin by a certain percent (for example a 25% decrease in potassium). If the patient's serum level of potassium is stable, then the amount of the toxin being excreted daily equals the intake for potassium, even in patients with CKD. Assuming that the cation exchanger equilibrates with colon concentrations of potassium similar to those we used in testing, the binding of potassium by H-ZP would be about 4 meq/gram in the colon. Since daily intake of potassium is about 50 meq, 25% of this amount would be 12.5 meq, and slightly over 3 grams of H-ZP would bind this amount of potassium in the colon. However, studies of intestinal concentrations of toxins like potassium show a wide range of concentrations, depending upon dietary intake, renal function, and levels of hormones such as aldosterone. The affinity term of Equation 2 allows calculation of the amount of potassium bound on the relevant sorbent at any concentration that is found to exist within the colon or small intestine. Note that in Table 8 we list separate affinities for binding of each toxin by H-ZP within the small intestine and colon. For toxins such as sodium which have the highest concentration in the small intestine the affinity calculated for small intestine should be used in estimating binding by H-ZP. With a daily intake of sodium of about 90 meq (2000 mg sodium), 14 grams of H-ZP would bind 100% of the daily intake, within the small intestine.

The affinity value can also be used to estimate the removal of essential cations. For example, calcium binding will probably occur mostly in the colon, where concentration of calcium is much higher than in the small intestine. Using the colon affinity term and assuming that the colon calcium concentrations are the same as those we tested, 20 grams of ingested H-ZP would bind about 20 meq of calcium daily. Therefore patients ingesting this amount of H-ZP should have food intake augmented by approximately 20 meq of calcium. If colon concentrations vary from those we tested, then the colon affinity term would allow calculation of a different bound amount of calcium.

Conclusions

1. The sorbent combination of H-ZP and OH-ZO has remarkably large capacity for binding uremic toxins, as demonstrated in tests that simulate the chemical composition of fluid within the small intestine and colon. For most sorbents taken orally, binding of uremic toxins is considered effective if approximately 1 meq/gram of the toxin is bound. In our in vitro tests of the ZP/ZO mixture binding of about 4 meq/gram of sodium and 1 meq/gram potassium occurred simultaneously in the small intestine solution, in addition to binding of calcium and magnesium (FIG. 7). In the colon solution, ZP/ZO bound about 4 meq/gram potassium and 0.5 meq/gram ammonium in addition to binding of calcium and magnesium (FIG. 8). Additionally, phosphate ($H_2PO_4$) binding was 2 meq/gram simultaneously with binding of chloride at about 2 meq/gram.

2. The total cation binding capacity of the ZP/ZO mixture demonstrated in our studies was much larger than expected. The maximum binding capacity of ZP is generally regarded to be 4 meq/gram, for any cations. In physiologic solutions such as those used in our testing, the binding of toxins is usually much less than this amount. In our tests, 6.77 to 8.06 meq/gram total cations were bound by H-ZP in combination with OH-ZO (Table 8). The large capacity of binding is important because for ZP, some sites will inevitably be filled by calcium and magnesium absorbed from the gut (up to 2 meq/gram for magnesium in the colon solution) (FIG. 8). The high total cation capacity means that binding of calcium and magnesium still allows capacity for binding other uremic toxins by the ZP. H-ZP can be partially loaded with calcium and magnesium before ingestion if desired to diminish removal of these divalent cations from the patient (as shown in FIG. 19). We have performed preliminary tests confirming that this H-ZP in combination with OH-ZO is mostly unimpeded in binding uremic toxins, and functions similar to H-ZP and OH-ZO but with less removal of calcium and magnesium.

3. The reason that H-ZP has high binding capacity for uremic toxins and a high total binding capacity in combination with OH-ZO is principally because hydroxide release from ZO decreases the concentration of the counter-ion hydrogen and maintains a neutral pH. When H-ZP alone was tested for binding of cations, pH was normalized with sodium hydroxide before testing the amount of cations bound. When pH was neutralized by sodium hydroxide, the H-ZP bound cations and uremic toxins with similar efficiency to the ZP/ZO combination. The affinities calculated for H-ZP in these tests was actually somewhat higher than the ZP/ZO combination. For every cation except sodium, the H-ZP and ZP/ZO mixture had higher affinity than demonstrated in the binary binding curves of the cations versus sodium on ZP (FIGS. 9-14). In the binary binding curve studies, pH was not controlled).

4. Balancing the pH of H-ZP is beneficial if it is used to bind cations within the intestine. Without the neutralization of hydrogen by hydroxide within the intestine, the patient would become acidotic. The normal urinary excretion of titratable acid in humans is about 50 meq/day. If 8 grams of H-ZP was ingested and exchanged hydrogen for cations within the intestine, this would add about 50 meq of acid to the patient, requiring double the usual urinary excretion of acid (which response is limited, especially in kidney failure). So, a vital function of the ZP/ZO mixture is the balancing of pH within the intestine. The contribution of hydroxide from the ZO occurs in a controlled, safe manner. Whenever a cation is absorbed by ZP, there is always a soluble anion in the gut for absorption to ZO. So the hydroxide is released from the ZO at the same time and place as hydrogen is released from ZP. If pH balancing of H-ZP was through addition of sodium hydroxide, for example, there would be uncontrolled release of hydroxide, raising pH very high in the stomach or small intestines. Further, the sodium released would function as a counter-ion to diminish binding of cations by the ZP. Finally, sodium would certainly be added to the intestinal fluid and to the patient, instead of being removed by the ZP/ZO mixture. In patients with edema and fluid overload, sodium is in excess and is in fact toxic. Its removal will be very helpful in treatment of CKD and ESRD.

5. Another important function of ZO in combination with ZP is in removal of phosphate. The combination of ZP/ZO always performs better than ZP alone in regard to phosphate binding. Phosphate removal is a frequent therapeutic goal and without ZO, the phosphate binding by ZP is very small. Current phosphate binders are of two types, either those that form covalent binding of phosphate (calcium and magnesium salts) or anion exchangers. Neither type is very well tolerated at high doses, and rarely does this therapy result in a normal serum phosphate level in patients with CKD or kidney failure. From our studies, 10 grams of OH-ZO could bind 30 meq of $H_2PO_4$ within the gut. This is slightly more than the daily ingested phosphate load of normal patients (800 mg phosphate).

6. The combination of ZP/ZO has both advantages and disadvantages as compared to ZS9/ZO. The advantage of the ZP mixture is greater capacity for potassium and phosphate. The ZP disadvantage is its capacity for calcium and magnesium, which are not desirable to remove from the patient and which are not bound by ZS9. Partially loading ZP with calcium and magnesium does reduce patient loss of these electrolytes to therapeutically acceptable levels (as shown in studies not reported here) while retaining capacity for potassium and other uremic toxins. With the ZS9/ZO combination, calcium and magnesium removal will not occur, so loading ZS9 with these divalent cations or replacing their loss will not be necessary. A further advantage of ZS9 is that since it is a crystal, there is no release of any soluble zirconium during its course through the gut. Zirconium has not been shown to be toxic in patients with kidney failure, even if serum levels are elevated (as occurred with use of the Sorb™ column for regenerating dialysate). The greatest disadvantage of ZS9 is that it is likely to be expensive. Since this compound was only recently approved for sale by FDA as an oral sorbent, the actual price is not known. ZP and ZO in highly purified form are available and quite inexpensive.

7. In our studies we have developed an empiric method to predict the binding of uremic toxins by the ZP/ZO sorbent mixture within the gut. The multi-component chemical concentrations of the small intestine and colon are quite different, and the actual concentrations vary widely in published studies. Further, the maximal rate of transfer of various uremic toxins from the patient's body to the gut is not known. We developed separate affinity values for the function of H-ZP in the small intestine and colon solutions. We can assume that the uremic toxin in question is bound principally in that portion of the gut with highest toxin concentration, and the binding affinity can be chosen appropriately. If the estimated intestinal concentration of the uremic toxin is determined to be higher or lower than what we used in testing, then using the affinity allows calculation of the amount of binding of the toxin by H-ZP. The total dose of H-ZP can be determined by the sum of amounts needed to bind each of the desired uremic toxins. This is probably an over-estimation of the amount needed, since each particle of H-ZP can actually bind several uremic toxins simultaneously.

8. Binary exchange data was useful in qualitatively predicting the comparative magnitude of the binding of each cation in the small intestine vs. colon conditions. Binary exchange data gave good quantitative estimates of multi-ion capacity of the sorbents for ammonium and sodium. In most cases, the binary binding curves significantly underestimated the actual performance of ZP/ZO mixtures in toxin binding. The theory of multi-component ion exchange is in evolution, and the binary exchange affinities should someday be useful to predict cation and anion exchange within complex environments such as intestinal fluids.

9. Overall, the studies we have done confirm that the combination of a hydrogen-loaded cation exchanger and hydroxide-loaded anion exchanger should be a very effective method of removing various uremic toxins. This function should help to maintain health of patients with ESRD, possibly delaying the need for dialysis in many patients. Also, the use of this sorbent mixture would obviate the need for many sorbents that patients with CKD already ingest to bind potassium, phosphate, and hydrogen (acid).

10. The removal of sodium by the mixed bed exchanger system raises the possibility that for the first time, our patients may have an active and very effective oral therapy to remove sodium. If sodium absorption is diminished, thirst will diminish and water intake will then diminish. Thus removal of sodium by mixed sorbent therapy may help to ameliorate fluid overload and edema in patients with CKD and ESRD.

11. The removal of ammonium from the gut by the mixed bed sorbent may be helpful by ameliorating high intestinal ammonium levels which occur in CKD and ESRD patients. High serum urea levels increase the normal transit of urea from serum to the gut, and hydrolysis of urea results in ammonium carbonate. Ammonium irritation of the gut is postulated to be one cause of increased gut permeability and elevated endotoxin levels in the serum of patients with CKD or ESRD. However, the binding of ammonium by the mixed sorbents shown in our studies is not large enough to make any significant change in the serum urea level of patients with kidney failure. The removal of ammonium may be much higher in patients taking the sorbent mixture than we expect, as we found in clinical studies of ZS9 for hyperkalemia. Additionally there are technical improvements which could vastly increase the ammonium removal by H-ZP or H-ZS9.

What is claimed:

1. A novel oral so bent therapy for removing uremic toxins from the gut comprised of:
   an ion exchanger mixture including a hydrogen-loaded cation exchanger and an hydroxide-loaded anion exchanger, wherein the cation exchanger is zirconium cyclosilicate or zirconium phosphate, wherein the anion exchanger is zirconium oxide, and
wherein the ratio of the hydrogen-loaded cation exchanger to the hydroxide-loaded anion exchanger is about 1:1.

2. The therapy of claim 1 wherein the cation exchanger is non-specific.

3. The therapy of claim 1 wherein the cation exchanger binds both monovalent and divalent cations.

4. The therapy of claim 1 wherein the hydrogen loaded cation exchanger is zirconium phosphate.

5. The therapy of claim 1 wherein the cation exchanger is selective for exchange of monovalent cations.

6. The therapy of claim 5 wherein the monovalent cations are selected from the group consisting of potassium, sodium and ammonium.

7. The therapy of claim 1 wherein the cation exchanger is zirconium, cyclosilicate.

8. The therapy of claim 1 wherein the anion exchanger is an inorganic compound.

9. The therapy of claim 8 wherein the anion exchanger is zirconium oxide.

10. The therapy of claim 1 wherein the amount and capacity of the cation exchanger can be increased versus the amount and capacity of the anion exchanger.

11. The therapy of claim 10 wherein the increase provides binding of monovalent cations and anions similar to that of the selective cation exchanger.

12. The therapy of claim 1 wherein amount of anion exchanger can be diminished to provide approximately equal ion exchange to the cation exchanger.

13. The therapy of claim 1 wherein the cation and anion exchangers are given in proportions to provide approximately equal binding capacity for anions and cations.

14. The therapy of claim 1 wherein the hydrogen-loaded cation exchanger is zirconium phosphate and the hydroxide-loaded anion exchanger is zirconium oxide.

* * * * *